US012807561B2

(12) United States Patent
Chen et al.

(10) Patent No.: US 12,807,561 B2
(45) Date of Patent: Nov. 24, 2026

(54) PHARMACEUTICAL SALT OF FINGOLIMOD, PREPARATION METHOD, PHARMACEUTICAL COMPOSITION AND USE THEREOF

(71) Applicant: Shanghai Yunsanova Biotechnology Co., Ltd, Shanghai (CN)

(72) Inventors: Zhixiang Chen, Shanghai (CN); Tao Zhu, Shanghai (CN); Lu Liu, Shanghai (CN); Tingting Wang, Shanghai (CN); Shuhuan Ying, Shanghai (CN)

(73) Assignee: Shanghai Yunsanova Biotechnology Co., Ltd, Shanghai (CN)

( * ) Notice: Subject to any disclaimer, the term of this patent is extended or adjusted under 35 U.S.C. 154(b) by 264 days.

(21) Appl. No.: 18/565,928

(22) PCT Filed: May 25, 2022

(86) PCT No.: PCT/CN2022/095013

§ 371 (c)(1),
(2) Date: Nov. 30, 2023

(87) PCT Pub. No.: WO2022/253077

PCT Pub. Date: Dec. 8, 2022

(65) Prior Publication Data

US 2024/0262783 A1 Aug. 8, 2024

(30) Foreign Application Priority Data

May 31, 2021 (CN) ......................... 202110601645.0

(51) Int. Cl.
*C07C 215/28* (2006.01)

(52) U.S. Cl.
CPC ........ *C07C 215/28* (2013.01); *C07B 2200/13* (2013.01); *C07C 2601/16* (2017.05)

(58) Field of Classification Search
CPC .............. C07C 215/28; C07C 2601/16; C07B 2200/13
See application file for complete search history.

(56) References Cited

FOREIGN PATENT DOCUMENTS

| | | | |
|---|---|---|---|
| CN | 1237906 | A | 12/1999 |
| CN | 102887829 | A | 1/2013 |
| EP | 2896609 | A1 | 7/2015 |
| JP | 2009529539 | A | 8/2009 |
| JP | 2014502251 | A | 1/2014 |
| JP | 2016532665 | A | 10/2016 |
| JP | 2020183382 | A | 11/2020 |
| WO | 2010055027 | A2 | 5/2010 |
| WO | 2010055028 | A2 | 5/2010 |
| WO | 2011009634 | A2 | 1/2011 |
| WO | WO 2011/009634 | * | 1/2011 |
| WO | 2012071524 | A1 | 5/2012 |
| WO | 2015015254 | A1 | 2/2015 |
| WO | 2020167845 | A1 | 8/2020 |
| WO | 2020245775 | A1 | 12/2020 |

OTHER PUBLICATIONS

Berge, Stephen M. et al., “Pharmaceutical Salts”, Journal of Pharmaceutical Sciences, vol. 66, No. 1, Jan. 1, 1977, p. 1-19.
Gould, Philip L. et al., “Salt selection for basic drugs”, International Journal of Pharmaceutics, vol. 33, No. 1-3, Nov. 1986, pp. 201-217.
Hirayama, Akira, “Handbook of organic compound crystal fabrication”, 2008, pp. 57-84.
Huang, Liang editor-in-chief; “Non-official translation: Long-Acting Preparations”; China Medical Encyclopedia, Editorial Committee of China Medical Encyclopedia; Shanghai Scientific & Technical Publishers; Oct. 31, 1988; pp. 63-64.

* cited by examiner

*Primary Examiner* — Marcos L Sznaidman
(74) *Attorney, Agent, or Firm* — NKL Law; Allen Xue

(57) ABSTRACT

A pharmaceutical salt of Fingolimod, preparation method, pharmaceutical composition and use thereof are provided. The pharmaceutical salt of Fingolimod of formula I is a salt formed from a Fingolimod free base and an organic acid having at least six carbon atoms. The pharmaceutical salt of Fingolimod has better solubility and stability, and a good market prospect.

I

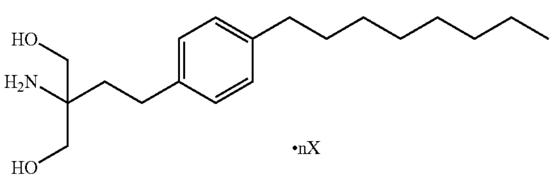

12 Claims, 16 Drawing Sheets

PHARMACEUTICAL SALT OF FINGOLIMOD, PREPARATION METHOD, PHARMACEUTICAL COMPOSITION AND USE THEREOF

CROSS-REFERENCE TO RELATED APPLICATIONS

The present application is a U.S. national stage entry of PCT International Application No. PCT/CN2022/095013, filed on May 25, 2022, which claims priority to Chinese Patent Application No. 202110601645.0, entitled "PHARMACEUTICAL SALT OF FINGOLIMOD, PREPARATION METHOD, PHARMACEUTICAL COMPOSITION AND USE THEREOF" filed with the China National Intellectual Property Administration on May 31, 2021, the content of each is incorporated herein by reference in its entirety.

TECHNICAL FIELD

The present disclosure relates to a pharmaceutically acceptable salt of Fingolimod, a method for preparing same, a pharmaceutical composition comprising same, and use thereof.

BACKGROUND

Multiple sclerosis (MS) is an autoimmune disease characterized primarily by inflammatory demyelinating diseases in the central nervous system, and has serious adverse effects on the activities, minds, and even mental states of patients. At present, the global incidence of MS is increasing year by year, with more than 2.5 million patients suffering. The prevalence in women is higher than that in men, and young people and children are among those affected.

Fingolimod is a sphingosine 1-phosphate receptor (S1PR) regulator having high immunosuppressive activity originally isolated from *Cordyceps sinclairii* and its close relative *Cordyceps sinensis*. The structurally modified Fingolimod hydrochloride (with a structure shown in formula II) is named FTY 720.

II

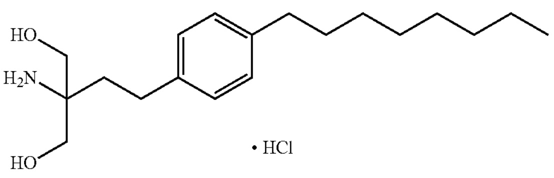

The Fingolimod hydrochloride capsule developed by Novartis, as the first oral preparation (capsule) for the treatment of MS in the world and the first drug for the treatment of MS in children, has a significant therapeutic effect in reducing the recurrence rate in patients with MS.

The inventors found in studies that Fingolimod hydrochloride has a high water solubility and an excessively high release rate after oral administration. Frequent administrations are required to maintain the plasma concentration, resulting in poor patient compliance. Patent No. WO2010055028A2 describes various crystalline forms of Fingolimod hydrochloride. However, those crystalline forms will undergo polymorphic transition due to changes in temperature, so that the stability of the crystalline forms of Fingolimod hydrochloride is poor, and changes in the crystalline forms affect the dissolution rate, bioavailability and the like and are thus unfavorable for the processability and stability of the preparation.

Therefore, to explore a pharmaceutically acceptable salt form of Fingolimod having low solubility, high stability, a good clinical effect and suitability for sustained-release administration and commercialization is an urgent technical problem to be solved at present.

SUMMARY

The present disclosure provides a salt of Fingolimod represented by formula I:

I

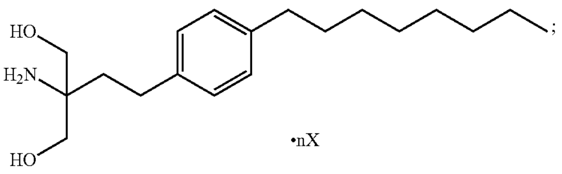

wherein X is an organic acid having six or more carbon atoms or an ester containing hydroxyl, and n is 0.5-2.0;

preferably, the salt is a pharmaceutically acceptable salt.

According to embodiments of the present disclosure, the organic acid having six or more carbon atoms may be selected from a C6-C30 organic acid, for example, a C6, C7, C8, C9, C10, C11, C12, C13, C14, C15, C16, C17, C18, C19, C20, C21, C22, C23, C24, C25, C26, C27, C28, C29, and C30 organic acid.

According to embodiments of the present disclosure, X is selected from one or more of the following substances comprising, but not limited to: hexanoic acid, heptanoic acid, octanoic acid, nonanoic acid, nonanedioic acid, decanoic acid, decanedioic acid, undecanoic acid, lauric acid (dodecanoic acid), tridecanoic acid, myristic acid (tetradecanoic acid), pentadecanoic acid, palmitic acid (i.e., hexadecanoic acid), heptadecanoic acid, stearic acid (octadecanoic acid), nonadecanoic acid, eicosanoic acid (arachidic acid), oleic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid (melissic acid), glyceric acid, xylonic acid, embonic acid (i.e., pamoic acid), 1-hydroxy-2-naphthoic acid, and naphthoic acid derivatives (comprising but not limited to naphthoates).

According to embodiments of the present disclosure, X is selected from one or more of embonic acid, 1-hydroxy-2-naphthoic acid, lauric acid, palmitic acid, decanedioic acid, undecanoic acid, and heptanoic acid.

According to embodiments of the present disclosure, n is 0.5, 1.0, or 2.0.

According to embodiments of the present disclosure, the salt of Fingolimod may be Fingolimod monopamoate (i.e., n=1.0, also known as Fingolimod monoembonate), Fingolimod hemipamoate (i.e., n=0.5, also known as Fingolimod hemiembonate), Fingolimod 1-hydroxy-2-naphthoate, Fingolimod laurate, Fingolimod palmitate, Fingolimod decanedioate, Fingolimod undecanoate, or Fingolimod heptanoate.

According to embodiments of the present disclosure, the salt of Fingolimod may be in a single-phase crystalline form, amorphous form, or mixed crystalline form.

According to embodiments of the present disclosure, the single-phase crystalline form refers to a structure consisting of a large number of microscopic units of matter (atoms, ions, molecules, etc.) arranged in an orderly manner according to certain rules, comprising crystalline forms of non-solvates (e.g., anhydrate) and solvates (e.g., hydrates) of the salt of Fingolimod.

According to embodiments of the present disclosure, the term “mixed crystalline form” refers to a mixture of different crystalline forms and/or other solid molecular forms of the same compound, for example, a solid comprising two or more crystalline forms and/or the amorphous form of the salt of Fingolimod.

According to embodiments of the present disclosure, the salt of Fingolimod comprises a solvate formed from the salt of Fingolimod and a solvent. For example, the solvate comprises a hydrate of the salt of Fingolimod and a solvate formed from the salt of Fingolimod and an organic solvent. Preferably, the “organic solvent” in the “solvate formed from the salt of Fingolimod and an organic solvent” comprises, but is not limited to, one or more of ethanol, acetone, and dimethylsulfoxide.

The present disclosure further provides a method for preparing the salt of Fingolimod, comprising the following step: performing a neutralization reaction on Fingolimod free base and X (i.e., an organic acid having six or more carbon atoms) to give the salt of Fingolimod.

According to embodiments of the present disclosure, the method may be performed with or without a solvent.

The present disclosure further provides another method for manufacturing the salt of Fingolimod, comprising the following steps: forming a solution by adding Fingolimod free base to an inorganic acid, forming a solution by adding X (i.e., an organic acid having six or more carbon atoms) to an inorganic base, and mixing the two solutions to give the salt of Fingolimod.

According to embodiments of the present disclosure, in the two methods described above, the organic acid having six or more carbon atoms may be a C6-C30 organic acid.

According to embodiments of the present disclosure, in the two methods described above, X is selected from one or more of the following substances comprising, but not limited to: hexanoic acid, heptanoic acid, octanoic acid, nonanoic acid, nonanedioic acid, decanoic acid, undecanoic acid, lauric acid (dodecanoic acid), tridecanoic acid, myristic acid (tetradecanoic acid), pentadecanoic acid, palmitic acid (hexadecanoic acid), heptadecanoic acid, stearic acid (octadecanoic acid), nonadecanoic acid, eicosanoic acid (arachidic acid), oleic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid (melissic acid), glyceric acid, xylonic acid, embonic acid (pamoic acid), 1-hydroxy-2-naphthoic acid, and naphthoic acid derivatives (comprising but not limited to naphthoates).

According to embodiments of the present disclosure, embonic acid is also known as pamoic acid, CAS No. 130-85-8.

The present disclosure further provides a crystalline form of a salt of Fingolimod, for example, a crystalline form of Fingolimod embonate and a crystalline form of Fingolimod 1-hydroxy 2-naphthoate.

According to embodiments of the present disclosure, the crystalline form of Fingolimod embonate is a crystalline form B of Fingolimod embonate comprising an X-ray powder diffraction pattern having characteristic peaks at 2θ of 3.3°±0.2°, 17.1°±0.2°, 21.8°±0.2°, etc.

Further, the crystalline form B of Fingolimod embonate has an X-ray powder diffraction pattern comprising characteristic peaks at 2θ of 3.3°±0.2°, 17.1°═0.2°, 18.7°±0.2°, 19.1°±0.2°, 21.8°±0.2°, 23.4°±0.2°, etc.

Further, the crystalline form B of Fingolimod embonate has an X-ray powder diffraction pattern comprising characteristic peaks at 2θ of 3.3°±0.2°, 17.1±0.2°, 17.7°═0.2°, 18.7°±0.2°, 19.1°±0.2°, 20.6°±0.2°, 21.8°±0.2°, 23.4°±0.2°, etc.

Furthermore, the crystalline form B of Fingolimod embonate has an X-ray powder diffraction pattern comprising absorption peaks at 2θ of 3.3°±0.2°, 7.1°±0.2°, 9.8±0.2°, 11.2°═0.2°, 11.8°±0.2°, 12.6°±0.2°, 13.5°±0.2°, 14.3°±0.2°, 14.7°±0.2°, 15.5°±0.2°, 16.1°±0.2°, 16.7°±0.2°, 17.1°±0.2°, 17.7°±0.2°, 18.7°±0.2°, 19.1°±0.2°, 19.6°±0.2°, 20.0°±0.2°, 20.6°±0.2°, 21.8°±0.2°, 22.6°±0.2°, 23.4°±0.2°, 23.8°±0.2°, 25.2°±0.2°, 26.5°±0.2°, 27.5°±0.2°, 30.1°±0.2°, etc.

According to embodiments of the present disclosure, the crystalline form B of Fingolimod embonate has an X-ray powder diffraction pattern substantially shown in FIG. 1.

According to one embodiment of the present disclosure, the crystalline form B of Fingolimod embonate has an X-ray powder diffraction pattern shown in Table 1.

According to embodiments of the present disclosure, the crystalline form B of Fingolimod embonate has a thermogravimetric analysis pattern substantially shown in FIG. 2.

According to embodiments of the present disclosure, the crystalline form B of Fingolimod embonate has a nuclear magnetic resonance spectrum substantially shown in FIG. 3.

According to embodiments of the present disclosure, in the crystalline form B of Fingolimod embonate, the molar ratio of Fingolimod to embonic acid is 1:0.5.

According to embodiments of the present disclosure, the crystalline form B of Fingolimod embonate is a hydrate.

According to embodiments of the present disclosure, the preparation method of the crystalline form B of Fingolimod embonate comprises:

mixing embonic acid with a solvent 1 to give an embonic acid solution; mixing Fingolimod hydrochloride with a solvent 2, adding the embonic acid solution, and stirring for reaction to give the crystalline form B of Fingolimod embonate;

wherein the solvent 1 is an alkaline solution, for example, an inorganic alkaline solution, preferably an aqueous potassium hydroxide solution;

the solvent 2 is water, methanol, ethanol, isopropanol, tetrahydrofuran, N,N-dimethylformamide, or a mixture of at least two of the foregoing solvents, preferably water.

According to embodiments of the present disclosure, the crystalline form of Fingolimod embonate is a crystalline form A of Fingolimod embonate.

According to embodiments of the present disclosure, the crystalline form A of Fingolimod embonate has an X-ray powder diffraction pattern comprising characteristic peaks at 2θ of 3.2°±0.2°, 19.3°±0.2°, 20.4°±0.2°, etc.

Further, the crystalline form A of Fingolimod embonate has an X-ray powder diffraction pattern comprising characteristic peaks at 2θ of 3.2°±0.2°, 9.6°±0.2°, 12.5°±0.2°, 18.5°±0.2°, 19.3°±0.2°, 20.4°±0.2°, etc.

Further, the crystalline form A of Fingolimod embonate has an X-ray powder diffraction pattern comprising characteristic peaks at 2θ of 3.2°±0.2°, 9.6°±0.2°, 12.5°±0.2°, 18.0°±0.2°, 18.5°±0.2°, 19.3°±0.2°, 20.4°±0.2°, 24.3°±0.2°, etc.

Furthermore, the crystalline form A of Fingolimod embonate has an X-ray powder diffraction pattern comprising characteristic peaks at 2θ of 3.2°±0.2°, 9.2°±0.2°, 9.6°±0.2°, 10.8°±0.2°, 11.6°±0.2°, 12.5°±0.2°, 13.1°±0.2°, 14.8°±0.2°, 15.1°±0.2°, 16.3°±0.2°, 18.0°±0.2°, 18.5°±0.2°, 19.3°±0.2°, 20.4°±0.2°, 21.6°±0.2°, 22.1°±0.2°, 22.6°±0.2°, 24.3°±0.2°, 25.2°±0.2°, etc.

According to embodiments of the present disclosure, the crystalline form A of Fingolimod embonate has an X-ray powder diffraction pattern substantially shown in FIG. 4.

According to one embodiment of the present disclosure, the crystalline form A of Fingolimod embonate has an X-ray powder diffraction pattern shown in Table 2.

According to embodiments of the present disclosure, the crystalline form A of Fingolimod embonate has a differential scanning calorimetry pattern substantially shown in FIG. 5. In one embodiment, the crystalline form A of Fingolimod embonate has two endothermic peaks and one exothermic peak. For example, the peak temperatures of the endothermic peaks are 128±5° C. and 180±5° C.; for example, the peak temperature of the exothermic peak is 153±5° C.

According to embodiments of the present disclosure, the crystalline form A of Fingolimod embonate has a thermogravimetric analysis pattern substantially shown in FIG. 6.

According to embodiments of the present disclosure, the crystalline form A of Fingolimod embonate is an anhydrate or a channel hydrate.

According to embodiments of the present disclosure, the crystalline form A of Fingolimod embonate has a nuclear magnetic resonance spectrum substantially shown in FIG. 7.

According to embodiments of the present disclosure, in the crystalline form A of Fingolimod embonate, the molar ratio of Fingolimod to embonic acid is 1:0.5.

According to embodiments of the present disclosure, the preparation method of the crystalline form A of Fingolimod embonate comprises:

drying the crystalline form B of Fingolimod embonate to give the crystalline form A of Fingolimod embonate;

wherein preferably, the drying is performed at 25-50° C., for example, 30° C. or 40° C.;

preferably, the drying is vacuum drying.

According to embodiments of the present disclosure, the crystalline form of Fingolimod embonate is a crystalline form I of Fingolimod embonate.

According to embodiments of the present disclosure, the crystalline form I of Fingolimod embonate has an X-ray powder diffraction pattern comprising characteristic peaks at 2θ of 3.0°±0.2°, 8.9°±0.2°, 19.9°±0.2°, etc.

Furthermore, the crystalline form I of Fingolimod embonate has an X-ray powder diffraction pattern comprising characteristic peaks at 2θ of 3.0°±0.2°, 3.3°±0.2°, 5.6±0.2°, 5.9°±0.2°, 6.9°±0.2°, 8.9°±0.2°, 9.8°±0.2°, 15.0°±0.2°, 16.2°±0.2°, 18.0°±0.2°, 18.8°±0.2°, 19.1°±0.2°, 19.6°±0.2°, 19.9°±0.2°, 21.0°±0.2°, 21.8°±0.2°, 25.2°±0.2°, etc.

Furthermore, the crystalline form I of Fingolimod embonate has an X-ray powder diffraction pattern substantially shown in FIG. 8.

According to one embodiment of the present disclosure, the crystalline form I of Fingolimod embonate has an X-ray powder diffraction pattern shown in Table 3.

According to embodiments of the present disclosure, the preparation method of the crystalline form I of Fingolimod embonate comprises:

mixing embonic acid with a solvent 1 to give an embonic acid solution;

mixing Fingolimod hydrochloride with a solvent 2, adding the embonic acid solution, stirring for reaction, filtering, and drying to give the crystalline form I of Fingolimod embonate;

wherein the solvent 1 is an alkaline solution, for example, an inorganic alkaline solution, preferably an aqueous potassium hydroxide solution;

the solvent 2 is water, methanol, ethanol, isopropanol, tetrahydrofuran, N,N-dimethylformamide, or a mixture of at least two of the foregoing solvents, preferably water.

According to embodiments of the present disclosure, the drying is performed for 2 to 7 days, preferably 2 days.

According to embodiments of the present disclosure, the crystalline form of Fingolimod embonate is a crystalline form J of Fingolimod embonate.

According to embodiments of the present disclosure, the crystalline form J of Fingolimod embonate has an X-ray powder diffraction pattern comprising characteristic peaks at 2θ of 3.2°±0.2°, 5.3°±0.2°, 10.1°±0.2°, 10.8°±0.2°, 18.1°±0.2°, 19.8°±0.2°, 20.6°±0.2°, 21.7°±0.2°, etc.

Furthermore, the crystalline form J of Fingolimod embonate has an X-ray powder diffraction pattern comprising characteristic peaks at 2θ of 3.2°±0.2°, 5.3°±0.2°, 6.3=0.2°, 9.5°±0.2°, 10.1°±0.2°, 10.8°±0.2°, 13.5°±0.2°, 17.0°±0.2°, 17.8°±0.2°, 18.1°±0.2°, 19.8°–0.2°, 20.6°±0.2°, 21.7°±0.2°, 22.0°±0.2°, 24.5°±0.2°, 25.5°±0.2°, etc.

Furthermore, the crystalline form J of Fingolimod embonate has an X-ray powder diffraction pattern substantially shown in FIG. 9.

According to one embodiment of the present disclosure, the crystalline form J of Fingolimod embonate has an X-ray powder diffraction pattern shown in Table 4.

According to embodiments of the present disclosure, the preparation method of the crystalline form J of Fingolimod embonate comprises:

standing the crystalline form I of Fingolimod embonate in a dry condition at room temperature to give the crystalline form J of Fingolimod embonate.

According to embodiments of the present disclosure, the crystalline form of Fingolimod embonate is a crystalline form C of Fingolimod embonate.

According to embodiments of the present disclosure, the crystalline form C of Fingolimod embonate has an X-ray powder diffraction pattern comprising characteristic peaks at 2θ of 3.2°±0.2°, 6.4°±0.2°, 19.8°±0.2°, etc.

Further, the crystalline form C of Fingolimod embonate has an X-ray powder diffraction pattern comprising characteristic peaks at 2θ of 3.2°±0.2°, 6.4°±0.2°, 9.6°±0.2°, 15.1°±0.2°, 19.8°±0.2°, 20.4°±0.2°, etc.

Further, the crystalline form C of Fingolimod embonate has an X-ray powder diffraction pattern comprising characteristic peaks at 2θ of 3.2°±0.2°, 6.4°±0.2°, 9.6°±0.2°, 13.6°±0.2°, 15.1°±0.2°, 15.6°±0.2°, 19.8°±0.2°, 20.4°±0.2°, etc.

Furthermore, the crystalline form C of Fingolimod embonate has an X-ray powder diffraction pattern comprising characteristic peaks at 2θ of 3.2°±0.2°, 5.4±0.2°, 6.4°±0.2°, 9.6°±0.2°, 12.8°±0.2°, 13.6°±0.2°, 14.3°±0.2°, 15.1°±0.2°, 15.6°±0.2°, 16.7°±0.2°, 17.3°±0.2°, 17.7°±0.2°, 18.3°±0.2°, 18.6°±0.2°, 19.0°±0.2°, 19.8°±0.2°, 20.4°–0.2°, 22.7°±0.2°, 23.1°–0.2°, 23.5°±0.2°, 25.9°±0.2°, 29.2°±0.2°, etc.

Furthermore, the crystalline form C of Fingolimod embonate has an X-ray powder diffraction pattern substantially shown in FIG. 10.

According to one embodiment of the present disclosure, the crystalline form C of Fingolimod embonate has an X-ray powder diffraction pattern shown in Table 5.

According to embodiments of the present disclosure, the preparation method of the crystalline form C of Fingolimod embonate comprises:

adding the crystalline form J of Fingolimod embonate to a solvent 3 to give a suspension, and stirring for crystallization to give the crystalline form C of Fingolimod embonate;

wherein the solvent 3 is a mixed solvent of n-heptane and ethyl acetate;

preferably, the stirring for crystallization is performed at 50-80° C., for example, 60° C.;

preferably, the stirring for crystallization is performed for 2-10 days, for example, 7 days;

preferably, the method further comprises: separating after the stirring for crystallization, and drying the separated solid to give the crystalline form C of Fingolimod embonate.

According to embodiments of the present disclosure, the crystalline form of Fingolimod embonate is a crystalline form D of Fingolimod embonate.

According to embodiments of the present disclosure, the crystalline form D of Fingolimod embonate has an X-ray powder diffraction pattern comprising characteristic peaks at 2θ of 3.3°±0.2°, 10.1°±0.2°, 20.3°±0.2°, etc.

Further, the crystalline form D of Fingolimod embonate has an X-ray powder diffraction pattern comprising characteristic peaks at 2θ of 3.3°±0.2°, 6.7°±0.2°, 10.1°±0.2°, 16.9°±0.2°, 18.8°±0.2°, 20.3°±0.2°, etc.

Further, the crystalline form D of Fingolimod embonate has an X-ray powder diffraction pattern comprising characteristic peaks at 2θ of 3.3°±0.2°, 6.7°±0.2°, 7.2°±0.2°, 10.1°±0.2°, 16.9°±0.2°, 18.8°±0.2°, 20.3°±0.2°, 23.8°±0.2°, etc.

Furthermore, the crystalline form D of Fingolimod embonate has an X-ray powder diffraction pattern comprising characteristic peaks at 2θ of 3.3°±0.2°, 5.0±0.2°, 6.7°±0.2°, 7.3°±0.2°, 8.9°±0.2°, 10.1°±0.2°, 10.5°±0.2°, 13.1°±0.2°, 13.5°±0.2°, 13.8°±0.2°, 15.5°±0.2°, 16.2°±0.2°, 16.9°±0.2°, 17.4°±0.2°, 17.8°±0.2°, 18.8°±0.2°, 19.5°±0.2°, 20.3°±0.2°, 22.2°±0.2°, 23.8°±0.2°, 25.7°±0.2°, 27.4°±0.2°, 29.1°±0.2°, etc.

According to embodiments of the present disclosure, the crystalline form D of Fingolimod embonate has an X-ray powder diffraction pattern substantially shown in FIG. 11.

According to one embodiment of the present disclosure, the crystalline form D of Fingolimod embonate has an X-ray powder diffraction pattern shown in Table 6.

According to embodiments of the present disclosure, the preparation method of the crystalline form D of Fingolimod embonate comprises:

dissolving the crystalline form B of Fingolimod embonate in a good solvent 1, and volatilizing for crystallization to give the crystalline form D of Fingolimod embonate.

The good solvent 1 is a mixed solvent of ethanol and water;

preferably, the volatilizing for crystallization is performed at room temperature.

According to embodiments of the present disclosure, the crystalline form of Fingolimod embonate is a crystalline form E of Fingolimod embonate.

According to embodiments of the present disclosure, the crystalline form E of Fingolimod embonate has an X-ray powder diffraction pattern comprising characteristic peaks at 2θ of 3.3°±0.2°, 17.3°±0.2°, 19.0°±0.2°, etc.

Further, the crystalline form E of Fingolimod embonate has an X-ray powder diffraction pattern comprising characteristic peaks at 2θ of 3.3°±0.2°, 9.8°±0.2°, 17.3°±0.2°, 17.7°±0.2°, 19.0°±0.2°, 21.8°±0.2°, etc.

Further, the crystalline form E of Fingolimod embonate has an X-ray powder diffraction pattern comprising characteristic peaks at 2θ of 3.3°±0.2°, 9.8°±0.2°, 17.3°±0.2°, 17.7°±0.2°, 19.0°±0.2°, 19.3°±0.2°, 20.0°±0.2°, 21.8°±0.2°, etc.

Furthermore, according to embodiments of the present disclosure, the crystalline form E of Fingolimod embonate has an X-ray powder diffraction pattern comprising characteristic peaks at 2θ of 3.3°±0.2°, 7.3°±0.2°, 7.5°±0.2°, 8.6°±0.2°, 8.9°±0.2°, 9.1°±0.2°, 9.8°±0.2°, 10.1°±0.2°, 10.5°±0.2°, 11.9°±0.2°, 13.1°±0.2°, 16.4°±0.2°, 17.1°±0.2°, 17.3°±0.2°, 17.7°±0.2°, 18.2°±0.2°, 19.0°±0.2°, 19.3°±0.2°, 20.0°±0.2°, 21.2°±0.2°, 21.8°±0.2°, 22.8°±0.2°, 23.2°±0.2°, 23.9°±0.2°, 24.3°±0.2°, etc.

According to embodiments of the present disclosure, the crystalline form E of Fingolimod embonate has an X-ray powder diffraction pattern substantially shown in FIG. 12.

According to one embodiment of the present disclosure, the crystalline form E of Fingolimod embonate has an X-ray powder diffraction pattern shown in Table 7.

According to embodiments of the present disclosure, the preparation method of the crystalline form E of Fingolimod embonate comprises:

dissolving the crystalline form B of Fingolimod embonate in a good solvent 2, and volatilizing for crystallization to give the crystalline form E of Fingolimod embonate.

The good solvent 2 is dioxane;

preferably, the volatilizing for crystallization is performed at 50-80° C., for example, 60° C.

According to embodiments of the present disclosure, the crystalline form of Fingolimod embonate is a crystalline form F of Fingolimod embonate.

According to embodiments of the present disclosure, the crystalline form F of Fingolimod embonate has an X-ray powder diffraction pattern comprising characteristic peaks at 2θ of 3.7°±0.2°, 18.0°±0.2°, 21.9°±0.2°, etc.

Further, the crystalline form F of Fingolimod embonate has an X-ray powder diffraction pattern comprising characteristic peaks at 2θ of 3.7°±0.2°, 9.2°±0.2°, 16.4°±0.2°, 17.0°±0.2°, 18.0°±0.2°, 19.7°±0.2°, 20.1°±0.2°, 21.9°±0.2°, etc.

Furthermore, the crystalline form F of Fingolimod embonate has an X-ray powder diffraction pattern comprising characteristic peaks at 2θ of 3.7°±0.2°, 8.0±0.2°, 9.2°±0.2°, 11.3°±0.2°, 16.4°±0.2°, 17.0°±0.2°, 18.0°±0.2°, 18.8°±0.2°, 19.7°±0.2°, 20.1°±0.2°, 21.9°±0.2°, etc.

According to embodiments of the present disclosure, the crystalline form F of Fingolimod embonate has an X-ray powder diffraction pattern substantially shown in FIG. 13.

According to one embodiment of the present disclosure, the crystalline form F of Fingolimod embonate has an X-ray powder diffraction pattern shown in Table 8.

According to embodiments of the present disclosure, the preparation method of the crystalline form F of Fingolimod embonate comprises:

adding the crystalline form B of Fingolimod embonate to a solvent 3 to give a slurry, and stirring for crystallization to give the crystalline form F of Fingolimod embonate;

wherein the solvent 3 is n-heptane, isopropyl acetate, or a mixed solvent thereof.

Preferably, the stirring for crystallization is performed at 50-80° C., for example, 60° C.

According to embodiments of the present disclosure, the crystalline form of Fingolimod embonate is a crystalline form G of Fingolimod embonate.

According to embodiments of the present disclosure, the crystalline form G of Fingolimod embonate has an X-ray powder diffraction pattern comprising characteristic peaks at 2θ of 3.6°±0.2°, 7.2°±0.2°, 19.9°±0.2°, etc.

Further, the crystalline form G of Fingolimod embonate has an X-ray powder diffraction pattern comprising characteristic peaks at 2θ of 3.6°±0.2°, 7.2°±0.2°, 18.1°±0.2°, 18.4°±0.2°, 19.9°±0.2°, 21.8°±0.2°, 22.6°±0.2°, 25.1°±0.2°, etc.

Furthermore, according to embodiments of the present disclosure, the crystalline form G of Fingolimod embonate has an X-ray powder diffraction pattern comprising characteristic peaks at 2θ of 3.6°±0.2°, 7.2°±0.2°, 9.0±0.2°, 9.5°±0.2°, 10.0°±0.2°, 11.2°±0.2°, 11.6°±0.2°, 11.8°±0.2°, 12.1°±0.2°, 13.1°±0.2°, 13.5°±0.2°, 15.1°±0.2°, 17.0°±0.2°, 18.1°±0.2°, 18.4°±0.2°, 18.9°±0.2°, 19.1°±0.2°, 19.9°±0.2°, 20.5°–0.2°, 20.9°±0.2°, 21.8°±0.2°, 22.6°±0.2°, 23.2°±0.2°, 23.9°–0.2°, 24.7°±0.2°, 25.1°±0.2°, 27.6°±0.2°, 28.1°±0.2°, etc.

According to embodiments of the present disclosure, the crystalline form G of Fingolimod embonate has an X-ray powder diffraction pattern substantially shown in FIG. 14.

According to one embodiment of the present disclosure, the crystalline form G of Fingolimod embonate has an X-ray powder diffraction pattern shown in Table 9.

According to embodiments of the present disclosure, the preparation method of the crystalline form G of Fingolimod embonate comprises:

adding the crystalline form B of Fingolimod embonate to a solvent 5 to give a slurry, and stirring for crystallization to give the crystalline form G of Fingolimod embonate;

wherein the solvent 5 is a mixed solvent of N,N-dimethylformamide and water.

According to embodiments of the present disclosure, the stirring for crystallization is performed at 50-80° C., for example, 60° C.

According to embodiments of the present disclosure, the crystalline form of Fingolimod embonate is a crystalline form H of Fingolimod embonate.

According to embodiments of the present disclosure, the crystalline form H of Fingolimod embonate has an X-ray powder diffraction pattern comprising characteristic peaks at 2θ of 3.3°±0.2°, 10.1°±0.2°, 17.2°±0.2°, etc.

Further, the crystalline form H of Fingolimod embonate has an X-ray powder diffraction pattern comprising characteristic peaks at 2θ of 3.3°±0.2°, 6.7°±0.2°, 10.1°±0.2°, 13.7°–0.2°, 17.2°–0.2°, 20.3°±0.2°, 20.6°±0.2°, etc.

Furthermore, the crystalline form H of Fingolimod embonate has an X-ray powder diffraction pattern comprising characteristic peaks at 2θ of 3.3°±0.2°, 5.0°±0.2°, 6.7±0.2°, 7.3°±0.2°, 10.1°±0.2°, 13.7°±0.2°, 17.2°±0.2°, 18.8°±0.2°, 20.3°±0.2°, 20.6°±0.2°, 21.8°±0.2°, 22.2°±0.2°, 23.7°±0.2°, 27.7°±0.2°, etc.

According to embodiments of the present disclosure, the crystalline form H of Fingolimod embonate has an X-ray powder diffraction pattern substantially shown in FIG. 15.

According to one embodiment of the present disclosure, the crystalline form H of Fingolimod embonate has an X-ray powder diffraction pattern shown in Table 10.

According to embodiments of the present disclosure, the preparation method of the crystalline form H of Fingolimod embonate comprises:

dissolving the crystalline form B of Fingolimod embonate in a good solvent 3, gradually adding an anti-solvent, and stirring for crystallization to give the crystalline form H of Fingolimod embonate.

The good solvent 3 is one or more of ethanol, isopropanol, dioxane, and dimethylsulfoxide, preferably ethanol;

the anti-solvent is water.

According to embodiments of the present disclosure, the crystalline form of Fingolimod embonate is a crystalline form K of Fingolimod embonate.

According to embodiments of the present disclosure, the crystalline form K of Fingolimod embonate has an X-ray powder diffraction pattern comprising characteristic peaks at 2θ of 3.4°±0.2°, 6.7°±0.2°, 7.3°±0.2°, 10.2°±0.2°, 10.5°±0.2°, 17.0°±0.2°, 18.9°±0.2°, 20.4°±0.2°, etc.

Furthermore, the crystalline form K of Fingolimod embonate van X-ray powder diffraction pattern comprising characteristic peaks at 2θ of 3.4°±0.2°, 6.7°±0.2°, 7.3=0.2°, 10.2°±0.2°, 10.5°±0.2°, 13.1°±0.2°, 13.8°±0.2°, 16.3°–0.2°, 17.0°±0.2°, 17.4°–0.2°, 17.9°–0.2°, 18.2°±0.2°, 18.9°±0.2°, 20.4°±0.2°, etc.

Furthermore, the crystalline form K of Fingolimod embonate has an X-ray powder diffraction pattern substantially shown in FIG. 16.

According to one embodiment of the present disclosure, the crystalline form K of Fingolimod embonate has an X-ray powder diffraction pattern shown in Table 11.

According to embodiments of the present disclosure, the preparation method of the crystalline form K of Fingolimod embonate comprises:

dissolving Fingolimod free base in a solvent 6, adding embonic acid, and stirring for reaction to give the crystalline form K of Fingolimod embonate;

wherein the solvent 6 is an alkyl acetate, for example, the alkyl is a C1-C5 alkyl; for example, the solvent 6 is one or more of ethyl acetate, isopropyl acetate, and n-butyl acetate, preferably n-butyl acetate.

According to embodiments of the present disclosure, the crystalline form of Fingolimod 1-hydroxy-2-naphthoate is a crystalline form 1 of Fingolimod 1-hydroxy-2-naphthoate.

According to embodiments of the present disclosure, the crystalline form 1 of Fingolimod 1-hydroxy-2-naphthoate has an X-ray powder diffraction pattern comprising characteristic peaks at 2θ of 3.2°±0.2°, 12.9°±0.2°, 19.4°±0.2°, etc.

Further, the crystalline form 1 of Fingolimod 1-hydroxy-2-naphthoate has an X-ray powder diffraction pattern comprising characteristic peaks at 2θ of 3.2°±0.2°, 9.6°±0.2°, 12.9°±0.2°, 16.1°±0.2°, 19.4°±0.2°, 25.9°±0.2°, etc.

Further, the crystalline form 1 of Fingolimod 1-hydroxy-2-naphthoate has an X-ray powder diffraction pattern comprising characteristic peaks at 2θ of 3.2°±0.2°, 9.6°±0.2°, 12.9°±0.2°, 16.1°±0.2°, 19.4°±0.2°, 25.9°±0.2°, 29.3°±0.2°, 36.0°±0.2°, etc.

Furthermore, the crystalline form 1 of Fingolimod 1-hydroxy-2-naphthoate has an X-ray powder diffraction pattern comprising absorption peaks at 2θ of 3.2°±0.2°, 6.4°±0.2°, 9.6±0.2°, 12.9°±0.2°, 13.9°±0.2°, 14.4°±0.2°, 15.7°±0.2°, 16.1°±0.2°, 16.5°±0.2°, 17.4°±0.2°, 18.3°±0.2°, 19.4°±0.2°, 20.0°±0.2°, 21.0°±0.2°, 21.6°±0.2°, 22.4°±0.2°, 23.5°±0.2°, 24.1°±0.2°, 25.1°±0.2°, 25.9°±0.2°, 29.3°±0.2°, 30.3°±0.2°, 32.6°±0.2°, 36.0°±0.2°, etc.

According to embodiments of the present disclosure, the crystalline form 1 of Fingolimod 1-hydroxy-2-naphthoate has an X-ray powder diffraction pattern substantially shown in FIG. 17.

According to one embodiment of the present disclosure, the crystalline form 1 of Fingolimod 1-hydroxy-2-naphthoate has an X-ray powder diffraction pattern shown in Table 12.

According to embodiments of the present disclosure, the crystalline form 1 of Fingolimod 1-hydroxy-2-naphthoate has a differential scanning calorimetry pattern substantially shown in FIG. 18; in one embodiment, the crystalline form 1 of Fingolimod 1-hydroxy-2-naphthoate has endothermic peaks at 125° C. and 144° C.

According to embodiments of the present disclosure, the crystalline form 1 of Fingolimod 1-hydroxy-2-naphthoate has a thermogravimetric analysis pattern substantially shown in FIG. 19. In one embodiment, the crystalline form 1 of Fingolimod 1-hydroxy-2-naphthoate has no weight loss before 120±5° C.

According to embodiments of the present disclosure, the crystalline form 1 of Fingolimod 1-hydroxy-2-naphthoate is an anhydrate.

According to embodiments of the present disclosure, the crystalline form 1 of Fingolimod 1-hydroxy-2-naphthoate has a nuclear magnetic resonance spectrum substantially shown in FIG. 20.

According to embodiments of the present disclosure, in the crystalline form 1 of Fingolimod 1-hydroxy-2-naphthoate, the molar ratio of Fingolimod to 1-hydroxy-2-naphthoic acid is 1:1.

According to embodiments of the present disclosure, the preparation method of the crystalline form 1 of Fingolimod 1-hydroxy-2-naphthoate comprises:

separately dissolving Fingolimod and 1-hydroxy-2-naphthoic acid in a solvent 7, and stirring for reaction to give the crystalline form 1 of Fingolimod 1-hydroxy-2-naphthoate;

wherein the solvent 7 is an alkyl acetate, for example, the alkyl is a C1-C5 alkyl; preferably, the solvent 7 is one or two or more of ethyl acetate, isopropyl acetate, n-butyl acetate, and isobutyl acetate, preferably ethyl acetate;

preferably, the stirring for reaction is performed at 25-80° C., preferably 40-60° C., and more preferably 60° C.;

preferably, the stirring for reaction refers to dropwise addition of a Fingolimod solution into a 1-hydroxy-2-naphthoic acid solution or dropwise addition of a 1-hydroxy-2-naphthoic acid solution into a Fingolimod solution.

The present disclosure further provides a pharmaceutical composition comprising the salt of Fingolimod and/or the crystalline form of the salt, and a pharmaceutically acceptable auxiliary material.

In the present disclosure, the pharmaceutical composition comprises, but is not limited to, a tablet, a capsule, a solution, a suspension, a (long-acting) injection, and a semisolid preparation, in order to facilitate the administration of compounds (i.e., active ingredients) to organisms such as human or other mammals, preferably an injection, and more preferably a long-acting injection.

According to embodiments of the present disclosure, the salt of Fingolimod and/or the crystalline form of the salt is at a concentration of not less than 15 mg/mL.

In the present disclosure, the pharmaceutically acceptable auxiliary material comprises one or more of a physiologically or pharmaceutically acceptable carrier, diluent, vehicle, and/or excipient.

According to embodiments of the present disclosure, the pharmaceutically acceptable auxiliary material may also be selected from one or more of a suspending agent, a wetting agent, an osmotic pressure regulator, a solvent, a stabilizer, a buffer, and a surfactant.

According to embodiments of the present disclosure, the suspending agent is at a concentration in the range of 0 mg/mL to 75 mg/mL, preferably 10 mg/mL to 75 mg/mL, for example, 30 mg/mL, 40 mg/mL, 50 mg/mL, or 75 mg/mL.

According to embodiments of the present disclosure, the suspending agent is selected from one or more of sodium carboxymethylcellulose, methylcellulose, polyethylene glycol 4000, and polyvinylpyrrolidone, preferably polyethylene glycol 4000.

According to embodiments of the present disclosure, the wetting agent is at a concentration in the range of 1 mg/mL to 10 mg/mL, preferably 1 mg/mL to 5 mg/mL, for example, 1 mg/mL, 1.5 mg/mL, 2.0 mg/mL, 2.5 mg/mL, 3.0 mg/mL, 3.5 mg/mL, 4.0 mg/mL, 4.5 mg/mL, or 5.0 mg/mL, preferably 1 mg/mL.

According to embodiments of the present disclosure, the wetting agent is selected from one or more of tween 20, tween 80, and poloxamer 188, preferably poloxamer 188.

According to embodiments of the present disclosure, the buffer is selected from one or more of phosphoric acid, phosphate, citric acid, sodium citrate, hydrochloric acid and sodium hydroxide.

According to embodiments of the present disclosure, the solvent is water, for example, water for injection.

As an example, the pharmaceutical composition may comprise:

(a) Fingolimod 1-hydroxy-2-naphthoate or a crystalline form thereof, for example, the crystalline form 1 of Fingolimod 1-hydroxy-2-naphthoate;

(b) polyethylene glycol 4000;

(c) poloxamer;

(d) disodium hydrogen phosphate;

(e) sodium dihydrogen phosphate; and (f) water for injection;

optionally, the pharmaceutical composition may comprise sodium hydroxide or hydrochloric acid.

The present disclosure further provides a method for preparing the pharmaceutical composition, comprising the following steps:

(1) dissolving a wetting agent, a buffer, and a suspending agent in a solvent;

(2) adding an appropriate amount of solvent to a sieved Fingolimod solid particle to fully wet and disperse the Fingolimod solid particle; and (3) diluting with a solvent to a target volume to give a suspension;

wherein the solvent is water, for example, water for injection.

According to embodiments of the present disclosure, the Fingolimod solid particle may be selected from Fingolimod, a pharmaceutically acceptable salt of Fingolimod, or a crystalline form of the salt.

According to embodiments of the present disclosure, the Fingolimod solid particle comprises, but is not limited to, Fingolimod embonate or a crystalline form thereof and Fingolimod 1-hydroxy-2-naphthoate or a crystalline form thereof.

According to embodiments of the present disclosure, in step (1), the wetting agent, the buffer, and the suspending agent may be sequentially dissolved in the solvent, for example, in water for injection.

According to embodiments of the present disclosure, in step (2), the Fingolimod solid particle may be sieved, for example, through a 400-mesh sieve.

The present disclosure further provides use of the pharmaceutically acceptable salt of Fingolimod in preparing a medicament for treating and/or preventing multiple sclerosis.

The present disclosure further provides a method for treating and/or preventing multiple sclerosis, comprising administering the pharmaceutical composition or medicament to a user.

The present disclosure further provides use of the pharmaceutical composition in preparing a medicament for treating and/or preventing multiple sclerosis.

Unless otherwise stated, the following terms used in the specification and claims of the present disclosure have the following meanings:

In the present disclosure, the terms "pharmaceutically acceptable", "carrier", "diluent", "vehicle", and "excipient" refer to such a substance (or substances) that may be comprised with a particular agent (active ingredients) to form a pharmaceutical composition, and that may be a solid or a liquid. The solid carrier comprises, but is not limited to, starch, calcium sulfate dihydrate, gypsum powder, talc, lactose, sucrose, mica, gelatin, agar, pectin, acacia, magnesium stearate, stearic acid, and the like. The liquid carrier comprises, but is not limited to, syrup, peanut oil, olive oil, saline solution, water, and the like. The carrier or diluent may comprise a material for delayed release or timed release known in the art, for example, glyceryl monostearate or glyceryl distearate used alone or in combination with a wax, ethylcellulose, hydroxypropyl methylcellulose, methyl methacrylate, and the like.

In the present disclosure, the term "solvate" refers to a molecular complex comprising a drug and a stoichiometric or non-stoichiometric amount of one or more solvent molecules (e.g., ethanol). When the solvent is closely associated with the drug, the resulting complex will have a well-defined stoichiometry independent of humidity. However, when the solvent is weakly associated with the drug, the solvent content will depend on humidity and drying conditions, as in channel solvates and hygroscopic compounds. In such a case, the complex will typically be non-stoichiometric.

In the present disclosure, the term "hydrate" describes a solvate comprising the drug and a stoichiometric or non-stoichiometric amount of water. The term "relative humidity" refers to the ratio of the amount of water vapor at a given temperature to the maximum amount of water vapor that can be maintained at that temperature and pressure, expressed as a percentage.

The preferred conditions described above may be combined arbitrarily to give preferred embodiments of the present disclosure without departing from the general knowledge in the art.

The reagents and starting materials used in the present disclosure are commercially available.

In the present disclosure, the room temperature refers to an ambient temperature of 10° C. to 35° C.

Advantageous Effects of Present Disclosure

The pharmaceutically acceptable salt of Fingolimod provided in the present disclosure has relatively good solubility and stability, thereby having a good commercial prospect. The defects that the water solubility and stability of Fingolimod hydrochloride are not satisfactory in the prior art are overcome.

The composition comprising the pharmaceutically acceptable salt of Fingolimod provided in the present disclosure has good stability, safety, and a long sustained release period.

DETAILED DESCRIPTION

Figure 1:
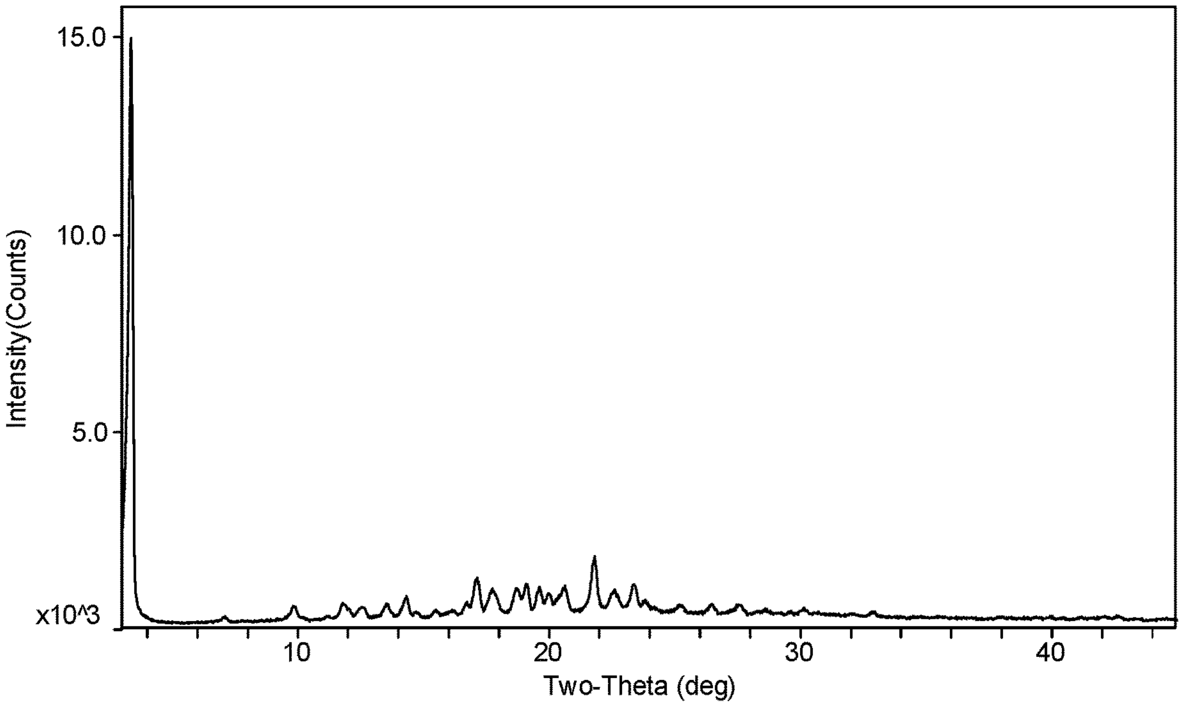
FIG. 1 is an XRPD pattern of the crystalline form B of Fingolimod embonate obtained in Example 1.

The embodiments of the present disclosure will be further illustrated in detail with reference to the following specific examples. It should be understood that the following examples are merely exemplary illustrations and explanations of the present disclosure, and should not be construed as limiting the protection scope of the present disclosure. All techniques implemented based on the content of the present disclosure described above are comprised within the protection scope of the present disclosure.

Unless otherwise stated, the starting materials and reagents used in the following examples are all commercially available products, or can be prepared using known methods.

Characterization and tests involved in the following examples:

The salt compounds in the examples were tested by nuclear magnetic resonance ($^1$H-NMR), with test parameters as follows:

The $^1$H-NMR measurements were conducted on a Bruker Advance III 500M nuclear magnetic resonance spectrometer at a frequency of 400 Mz with deuterated DMSO as the solvent.

X-Ray Powder Diffractometer (XRPD)

The XRPD measurements were conducted on a Bruker model D8 Advance X-ray powder diffractometer using a round zero background single crystal silicon sample stage. The scan parameters are as follows: voltage: 40 kV; current: 40 mA; scan range: 3-45°; scan increment: 0.02°; scan mode: continuous scan.

Differential Scanning calorimetry (DSC)

The DSC measurements were conducted on a TA Instruments Q2000 sealed pan device: samples (about 1-2 mg) were measured out in aluminum pans and transferred to the instrument for measurement. Test parameters are as follows: the instrument was equilibrated at 30° C. and heated at a rate of 10° C./min, and the experiments were conducted in a nitrogen atmosphere.

Thermogravimetric Analysis (TGA)

The TGA measurements were conducted on a TA Instruments Q2000 device: samples (about 2-5 mg) were measured out in platinum pans and transferred to the instrument for measurement. The test parameters are as follows: the instrument was heated at a rate of 10° C./min, and the experiments were conducted in a nitrogen atmosphere.

Method for Detecting Related Substances by HPLC

| | | | |
|---|---|---|---|
| Instrument | High-performance liquid chromatograph | | |
| Chromatographic column | YMC-Pack ODS-AQ 4.6 mm × 250 mm, 5 μm | | |
| Mobile phase A | 0.1% aqueous phosphoric acid solution | Mobile phase B | Acetonitrile |
| | Time (min) | Mobile phase A (%) | Mobile phase B (%) |
| Elution gradient | 0.0 | 80 | 20 |
| | 20.0 | 5 | 95 |
| | 23.0 | 5 | 95 |
| | 23.1 | 80 | 20 |
| | 33.0 | 80 | 20 |
| Detection wavelength | 215 nm | Flow rate | 0.8 mL/min |
| Column temperature | 40° C. | Injection volume | 10 μL |

Example 1: Preparation of Crystalline Form B of Fingolimod Embonate

Step 1: 292 mg of potassium hydroxide was taken, and 5 mL of water was added to give a potassium hydroxide solution.

Step 2: 78 mg of embonic acid was taken, and 1 mL of water was added. The mixture was stirred for dispersion before 0.4 mL of potassium hydroxide solution was added. The resulting mixture was stirred and filtered to give an embonic acid solution.

Step 3: 68 mg of Fingolimod hydrochloride was taken, and 1 mL of water was added. The mixture was stirred for complete dissolution before 0.6 mL of the embonic acid solution obtained in step 2 was added. The mixture was stirred for reaction. Another 7 mL of water was added, and the mixture was stirred for 30 min. Another 0.2 mL of the embonic acid solution obtained in step 2 was added for reaction for another 30 min. The resulting mixture was filtered to give Fingolimod embonate, which was confirmed by XRPD to be the crystalline form B of Fingolimod embonate.

The XRPD pattern of the crystalline form B of Fingolimod embonate is shown in FIG. 1;

The XRPD analysis of the crystalline form B of Fingolimod embonate is shown in Table 1:

TABLE 1

| 2θ/° | Relative intensity I/% |
|---|---|
| 3.262 | 100 |
| 7.103 | 1.8 |
| 9.829 | 4.5 |
| 11.241 | 0.8 |
| 11.8 | 4.6 |
| 12.59 | 2.7 |
| 13.519 | 3.7 |
| 14.327 | 6 |
| 14.7 | 1.4 |
| 15.489 | 1.7 |
| 16.123 | 1.5 |
| 16.732 | 2.9 |
| 17.128 | 9.9 |
| 17.741 | 6.6 |
| 18.67 | 6.8 |
| 19.064 | 7.7 |
| 19.614 | 6 |
| 19.971 | 5 |
| 20.621 | 6.5 |
| 21.825 | 16.1 |
| 22.615 | 5.3 |
| 23.385 | 7.2 |

TABLE 1-continued

| 2θ/° | Relative intensity I/% |
|---|---|
| 23.838 | 2.8 |
| 25.217 | 2.1 |
| 26.482 | 2.6 |
| 27.512 | 2.7 |
| 30.118 | 2 |

Figure 2:
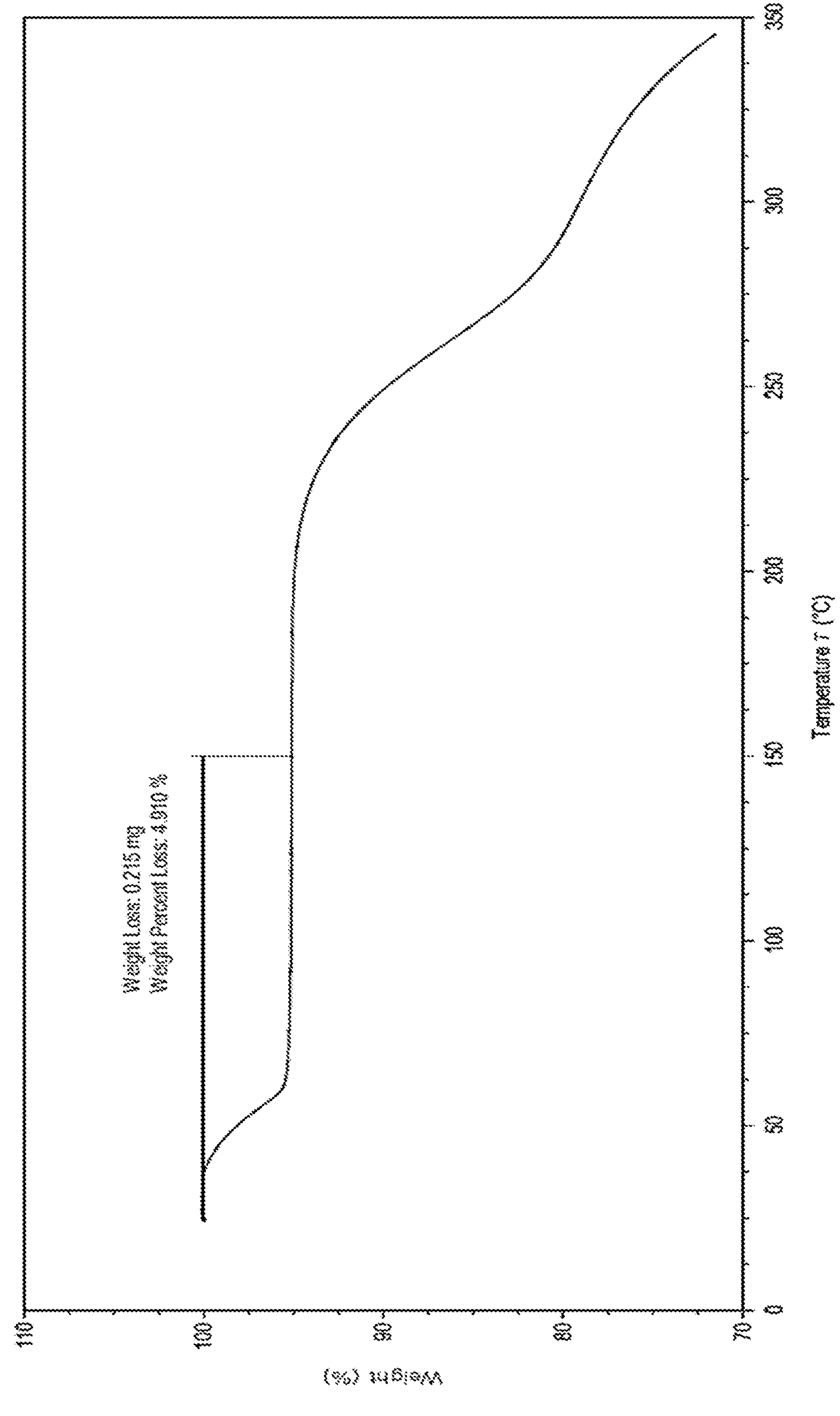
FIG. 2 is a TGA pattern of the crystalline form B of Fingolimod embonate obtained in Example 1.
Figure 3:
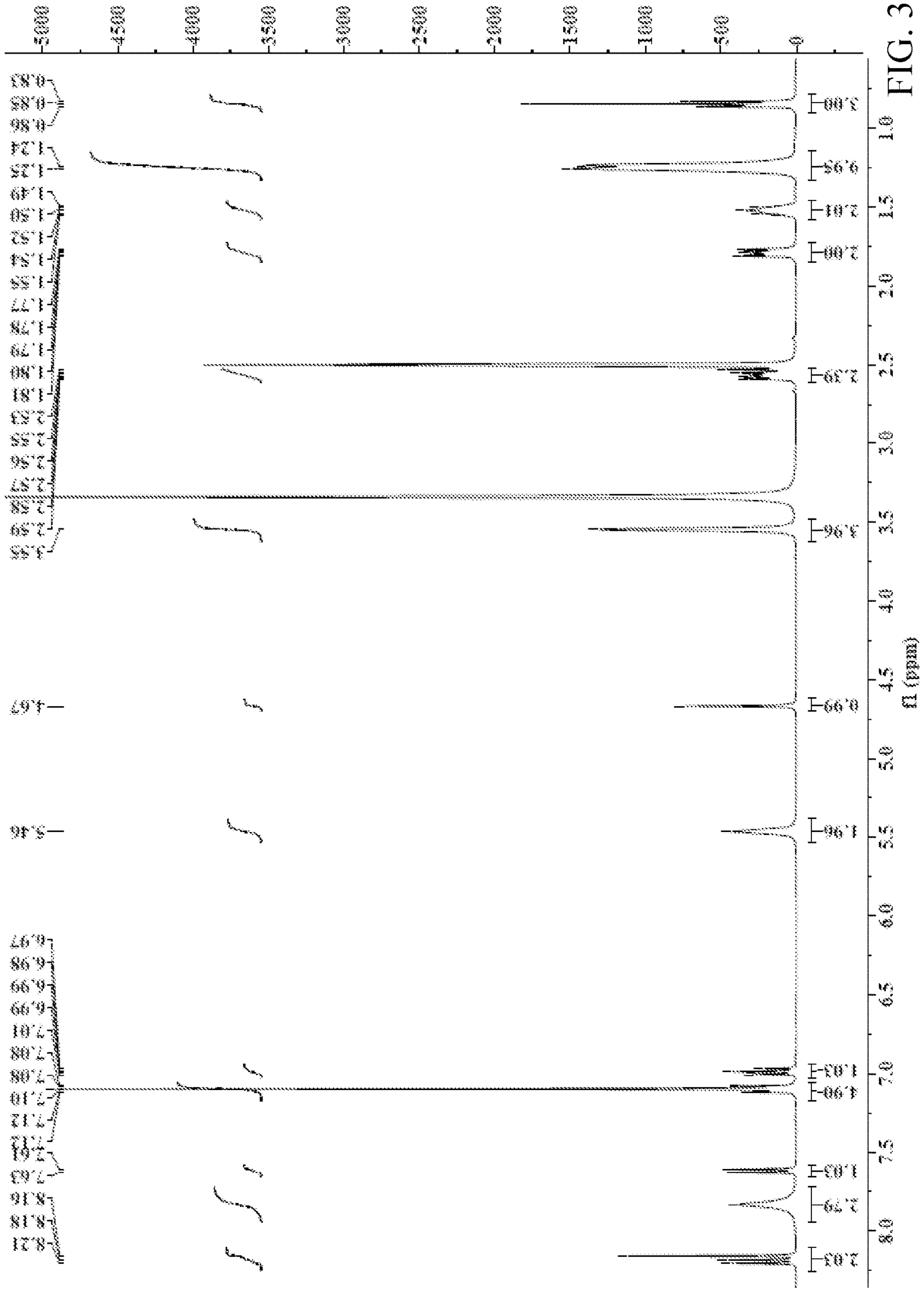
FIG. 3 is a $^1$H-NMR spectrum of the crystalline form B of Fingolimod embonate obtained in Example 1.

A TGA pattern of the crystalline form B of Fingolimod embonate is shown in FIG. 2;

A $^1$H-NMR spectrum of the crystalline form B of Fingolimod embonate is shown in FIG. 3, $^1$H-NMR (400 MHz, DMSO-d6): δ8.21-8.16 (t, 2H), 7.83 (s, 3H), 7.62 (d, 2H), 7.10 (m, 5H), 6.99 (m, 1H), 5.46 (s, 2H), 4.67 (s, 1H), 3.55 (s, 4H), 2.56 (m, 2H), 1.79 (m, 2H), 1.52 (m, 2H), 1.24 (d, 10H), 0.86-0.83 (t, 3H), indicating that the molar ratio of Fingolimod free base to embonic acid is about 1:0.5.

Example 2: Preparation of Crystalline Form B of Fingolimod Embonate

Step 1: 5.84 g of potassium hydroxide was taken, and 100 mL of water was added to give a potassium hydroxide solution.

Step 2: 15.6 g of embonic acid was taken, and 200 ml of water was added. The mixture was stirred for dispersion before 80 mL of potassium hydroxide solution was added. The resulting mixture was stirred and filtered to give an embonic acid solution.

Step 3: 13.6 g of Fingolimod hydrochloride was taken, and 200 mL of water was added. The mixture was stirred for complete dissolution before 120 mL of the embonic acid solution obtained in step 2 was added. The mixture was stirred for reaction. Another 1400 mL of water was added, and the mixture was stirred for 30 min. Another 40 mL of the embonic acid solution obtained in step 2 was added for reaction for another 30 min. The resulting mixture was filtered to give Fingolimod embonate, which was confirmed by XRPD to be the crystalline form B of Fingolimod embonate.

Example 3: Preparation of Crystalline Form a of Fingolimod Embonate 10 g of the crystalline form B of Fingolimod embonate prepared in Example 2 was dried in vacuum overnight at 40° C. to give the crystalline form A of Fingolimod embonate.

Figure 4:
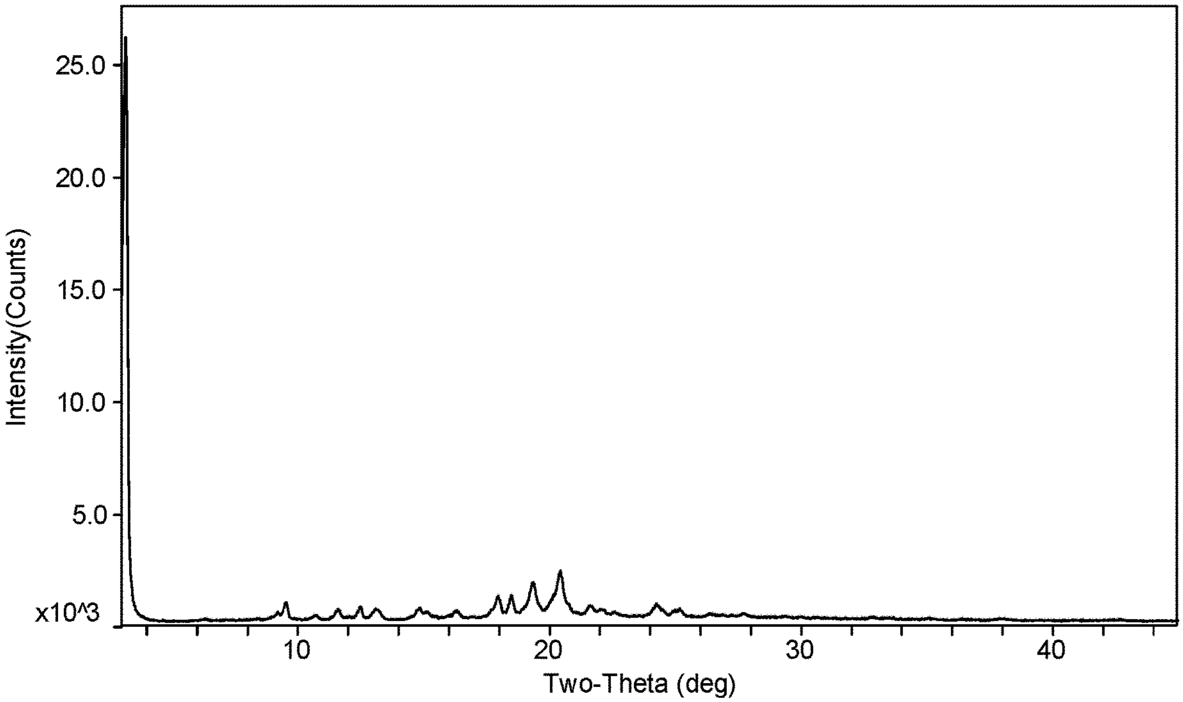
FIG. 4 is an XRPD pattern of the crystalline form A of Fingolimod embonate obtained in Example 3.

The XRPD pattern of the crystalline form A of Fingolimod embonate is shown in FIG. 4;

The XRPD analysis of the crystalline form A of Fingolimod embonate is shown in Table 2:

TABLE 2

| 2θ/° | Relative intensity I/% |
|---|---|
| 3.158 | 100 |
| 9.197 | 1.3 |
| 9.55 | 2.9 |
| 10.754 | 0.7 |
| 11.604 | 1.6 |
| 12.492 | 1.9 |
| 13.104 | 1.7 |
| 14.84 | 1.8 |
| 15.136 | 1.1 |
| 16.302 | 1.3 |
| 17.957 | 2.8 |
| 18.489 | 3 |

TABLE 2-continued

| 2θ/° | Relative intensity I/% |
|---|---|
| 19.339 | 4.8 |
| 20.424 | 7 |
| 21.61 | 1.4 |
| 22.064 | 1 |
| 22.594 | 0.5 |
| 24.253 | 2 |
| 25.182 | 1.2 |

Figure 5:
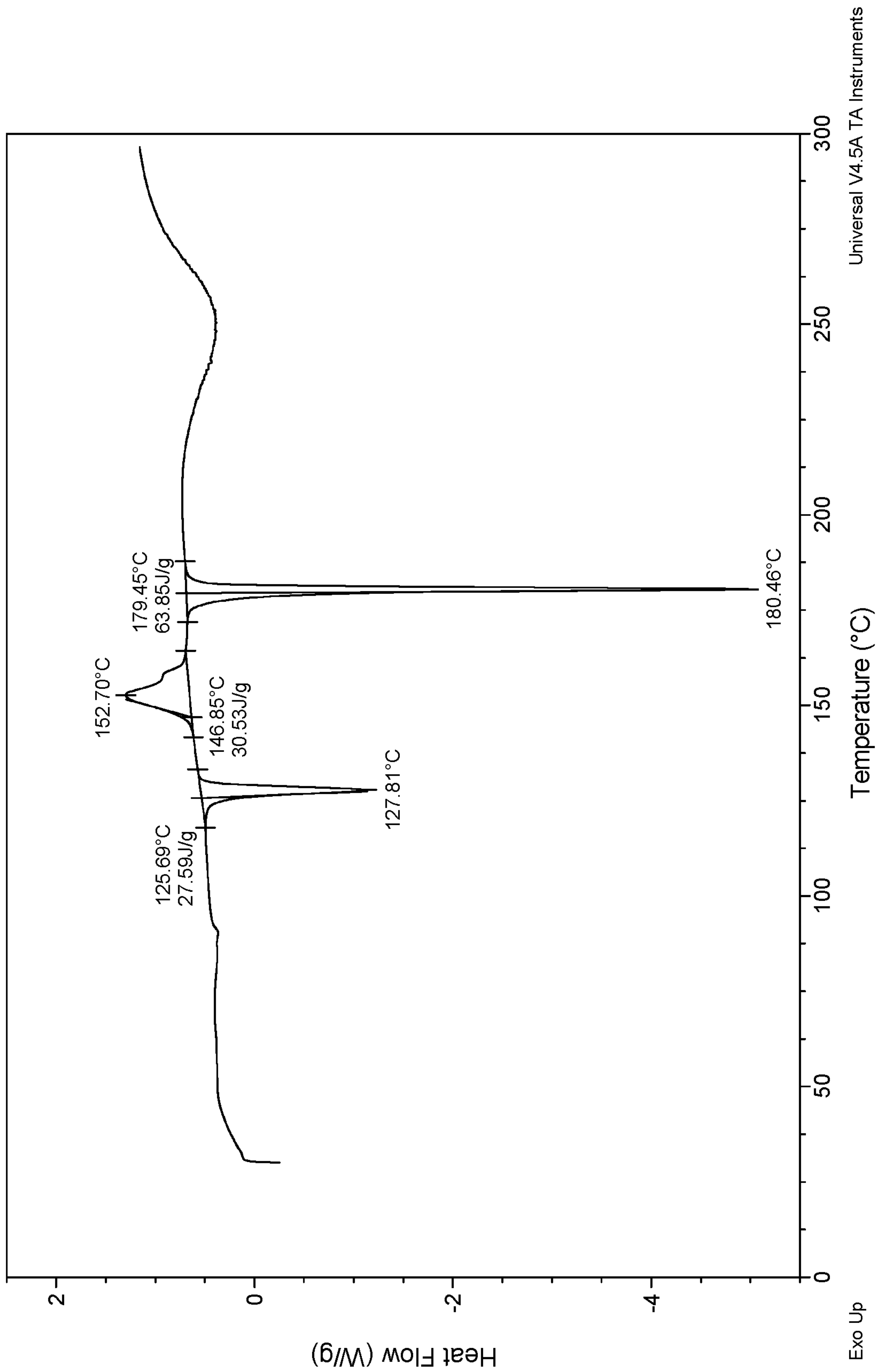
FIG. 5 is a DSC pattern of the crystalline form A of Fingolimod embonate obtained in Example 3.
Figure 6:
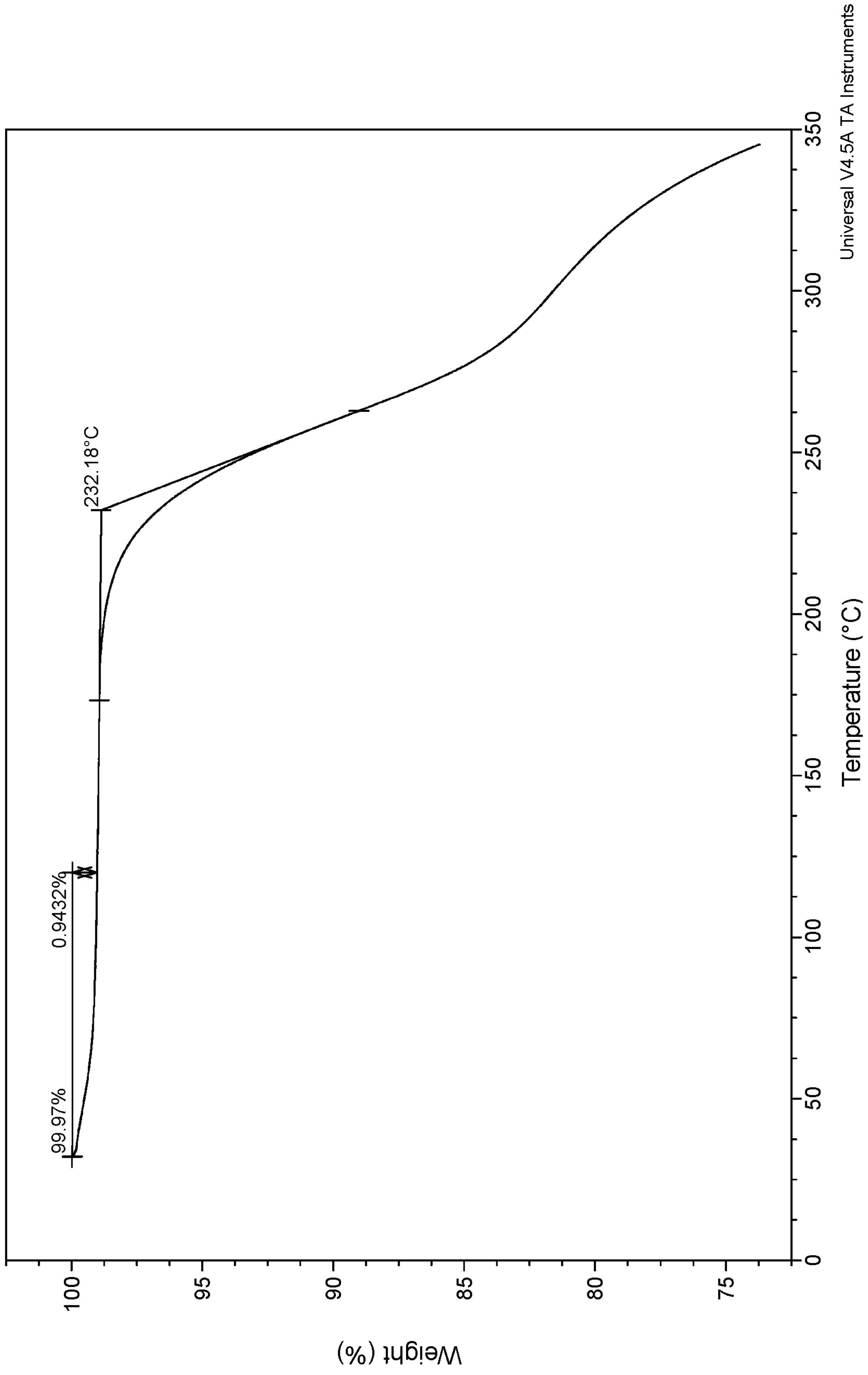
FIG. 6 is a TGA pattern of the crystalline form A of Fingolimod embonate obtained in Example 3.
Figure 7:
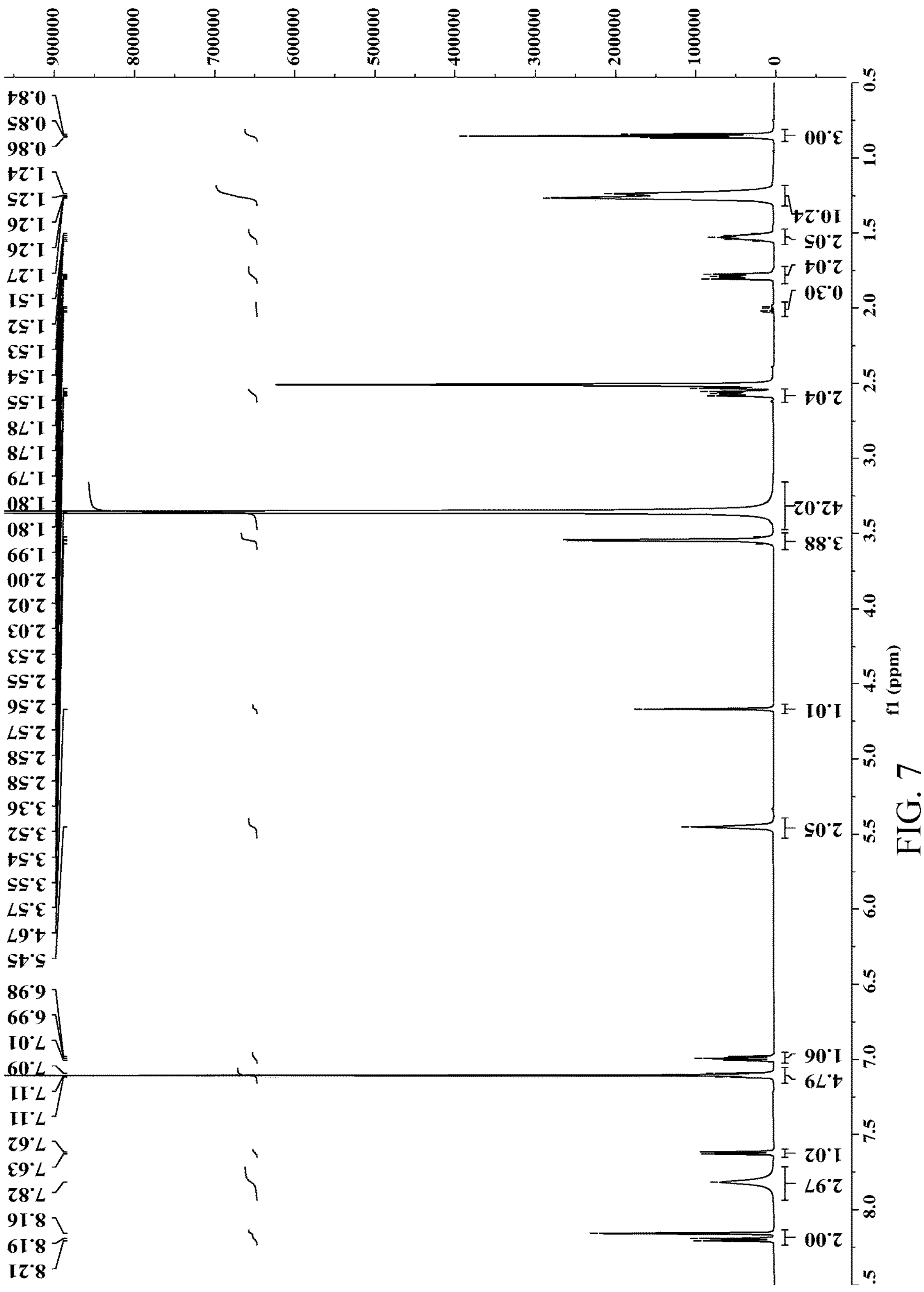
FIG. 7 is a $^1$H-NMR spectrum of the crystalline form A of Fingolimod embonate obtained in Example 3.

A DSC pattern of the crystalline form A of Fingolimod embonate is shown in FIG. 5;

A TGA pattern of the crystalline form A of Fingolimod embonate is shown in FIG. 6;

A $^1$H-NMR spectrum of the crystalline form A of Fingolimod embonate is shown in FIG. 7, indicating that the molar ratio of Fingolimod free base to embonic acid is about 1:0.5.

Example 4: Preparation of Crystalline Form I of Fingolimod Embonate

Step 1: 1192.23 mg of potassium hydroxide was taken and dissolved in 20 mL of water to give an aqueous potassium hydroxide solution at a concentration of about 1.062 mmol/mL.

Step 2: 3124 mg of embonic acid was taken, and 20 mL of water was added. The mixture was stirred for dispersion before 16.725 mL of aqueous potassium hydroxide solution was added. The resulting mixture was stirred for 1 h and filtered, and the filtrate was collected to give a potassium embonate solution.

Step 3: Preparation of Fingolimod hydrochloride solution: 2721 mg of Fingolimod hydrochloride was taken, and 60 mL of water was added. The mixture was stirred for substantially complete dissolution, and the resulting mixture was filtered to collect the filtrate.

Step 4: 20.990 mL of potassium embonate solution was added slowly to the Fingolimod hydrochloride solution under stirring. The mixture was stirred overnight at room temperature and filtered in vacuum, and the filtrate was dried in vacuum at 35° C. for 2 days to give a hemiembonate, which was confirmed by XRPD to be the crystalline form I of Fingolimod embonate.

Figure 8:
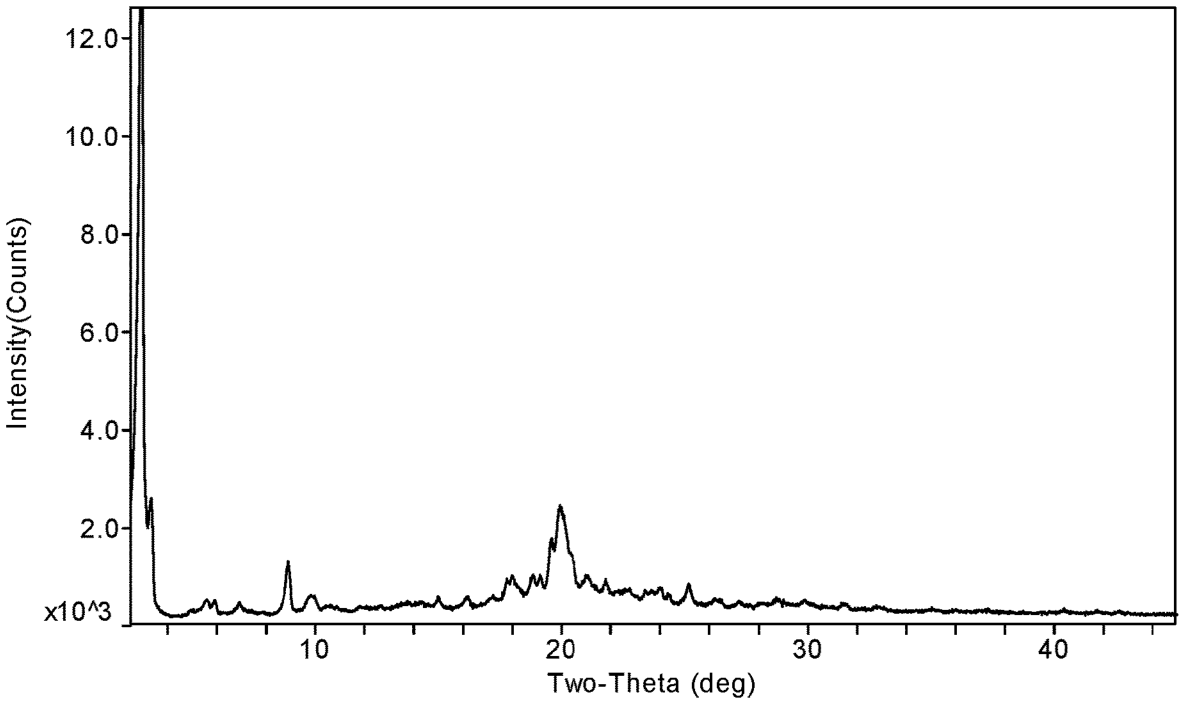
FIG. 8 is an XRPD pattern of the crystalline form I of Fingolimod embonate obtained in Example 4.

The XRPD pattern of the crystalline form I of Fingolimod embonate is shown in FIG. 8.

The XRPD analysis of the crystalline form I of Fingolimod embonate is shown in Table 3:

TABLE 3

| 2θ/° | Relative intensity I/% |
|---|---|
| 2.953 | 100 |
| 3.348 | 14.2 |
| 5.598 | 1.7 |
| 5.915 | 1.5 |
| 6.919 | 1.3 |
| 8.913 | 6.1 |
| 9.821 | 1.7 |
| 14.995 | 1.2 |
| 16.175 | 1.2 |
| 17.991 | 2.5 |
| 18.838 | 1.9 |
| 19.118 | 1.6 |
| 19.589 | 5.8 |
| 19.925 | 9.7 |

TABLE 3-continued

| 2θ/° | Relative intensity I/% |
|---|---|
| 20.994 | 1.5 |
| 21.803 | 1.7 |
| 25.174 | 2.4 |

Example 5: Preparation of Crystalline Form J of Fingolimod Embonate

A sample of the crystalline form I of Fingolimod embonate prepared in Example 4 was taken and dried at room temperature for 10 days to give a crystalline form J of Fingolimod embonate.

Figure 9:
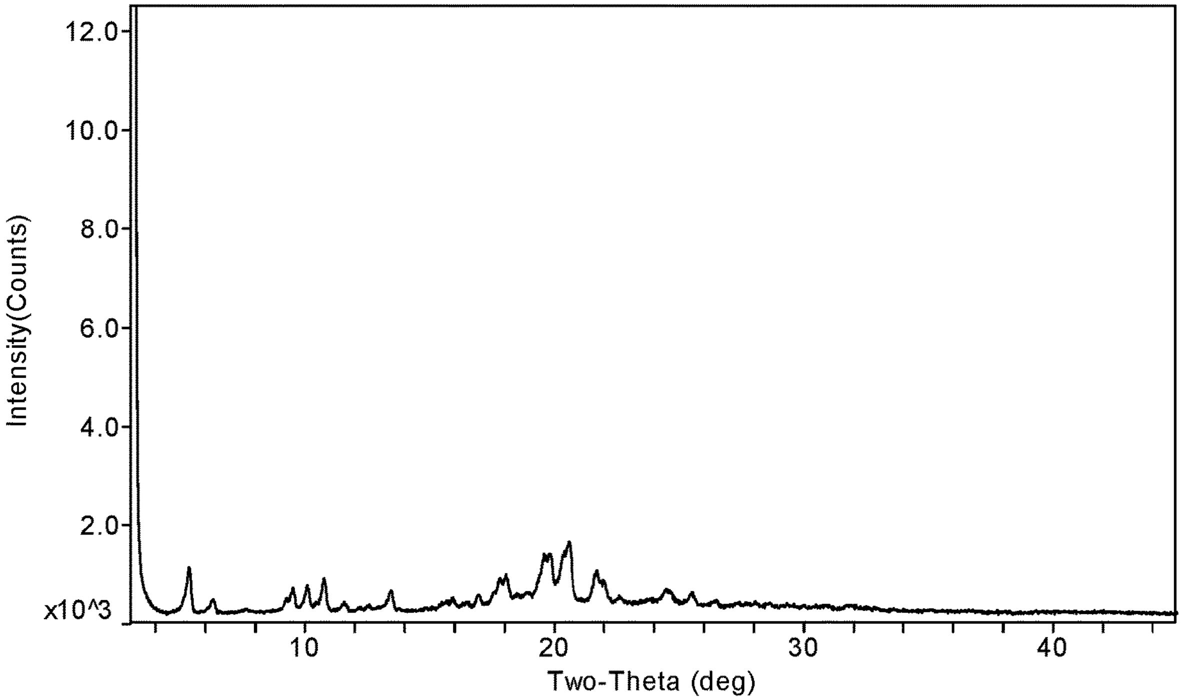
FIG. 9 is an XRPD pattern of the crystalline form J of Fingolimod embonate obtained in Example 5.

The XRPD pattern of the crystalline form J of Fingolimod embonate is shown in FIG. 9.

The XRPD analysis of the crystalline form J of Fingolimod embonate is shown in Table 4:

TABLE 4

| 2θ/° | Relative intensity I/% |
|---|---|
| 3.157 | 100 |
| 5.349 | 3.3 |
| 6.315 | 1 |
| 9.53 | 1.5 |
| 10.103 | 1.8 |
| 10.775 | 2.2 |
| 13.459 | 1.4 |
| 16.952 | 0.8 |
| 17.819 | 1.6 |
| 18.056 | 1.8 |
| 19.775 | 2.9 |
| 20.564 | 3.6 |
| 21.726 | 2.3 |
| 21.965 | 1.6 |
| 24.491 | 1 |
| 25.517 | 0.8 |

Example 6: Preparation of Crystalline Form C of Fingolimod Embonate 210 mg of a sample of the crystalline form J of Fingolimod embonate prepared in Example 5 was taken, and 3.5 mL of n-heptane and 3.5 mL of ethyl acetate were added. The mixture was stirred at 60° C. for 7 days, centrifuged, and dried in vacuum at 40° C. for 4 h to give the crystalline form C of Fingolimod embonate.

Figure 10:
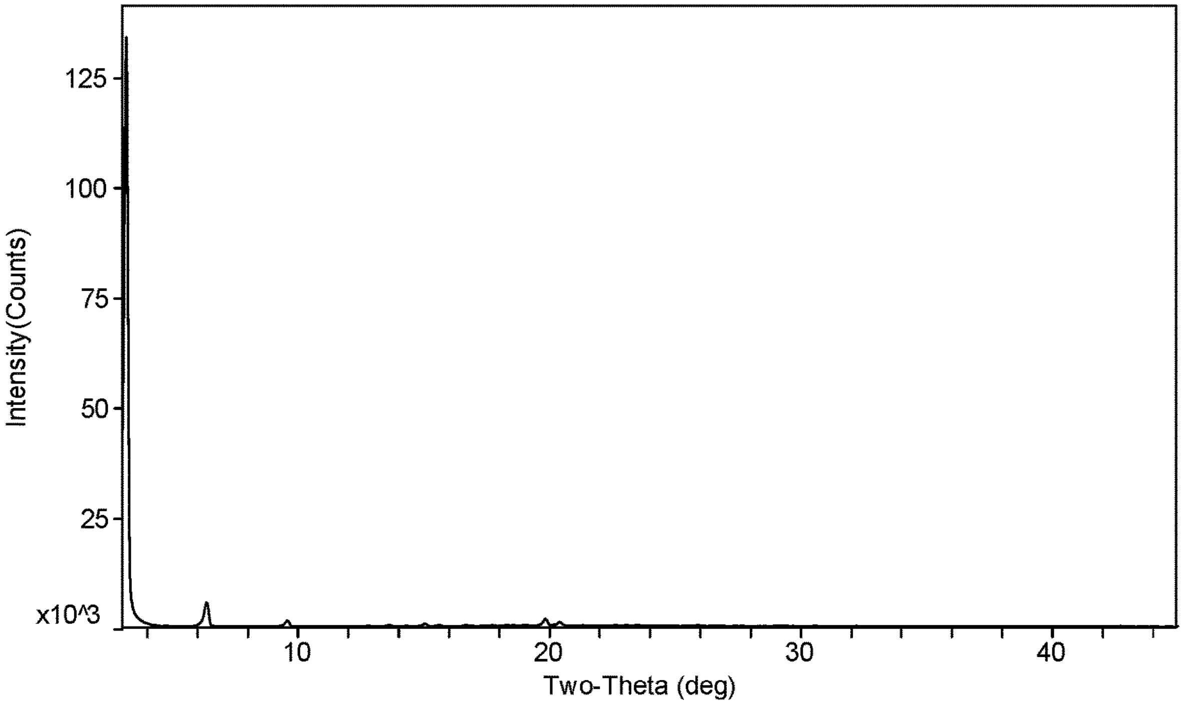
FIG. 10 is an XRPD pattern of the crystalline form C of Fingolimod embonate obtained in Example 6.

The XRPD pattern of the crystalline form C of Fingolimod embonate is shown in FIG. 10.

The XRPD analysis of the crystalline form C of Fingolimod embonate is shown in Table 5:

TABLE 5

| 2θ/° | Relative intensity I/% |
|---|---|
| 3.176 | 100 |
| 5.383 | 0.1 |
| 6.355 | 4.1 |
| 9.573 | 1 |
| 12.845 | 0.1 |
| 13.599 | 0.2 |
| 14.293 | 0.1 |
| 15.056 | 0.5 |
| 15.61 | 0.2 |
| 16.676 | 0.2 |
| 17.324 | 0.1 |
| 17.738 | 0.1 |

TABLE 5-continued

| 2θ/° | Relative intensity I/% |
|---|---|
| 18.311 | 0.2 |
| 18.57 | 0.2 |
| 19.042 | 0.1 |
| 19.815 | 1.2 |
| 20.403 | 0.6 |
| 22.652 | 0.2 |
| 23.089 | 0.1 |
| 23.522 | 0.2 |
| 25.909 | 0.2 |
| 29.206 | 0.1 |

Example 7: Preparation of Crystalline Form D of Fingolimod Embonate 25 mg of a sample of the crystalline form B of Fingolimod embonate prepared in Example 3 was taken, and 0.3 mL of ethanol and 0.1 mL of water were added. The resulting mixture was volatilized at room temperature to give the crystalline form D of Fingolimod embonate.

Figure 11:
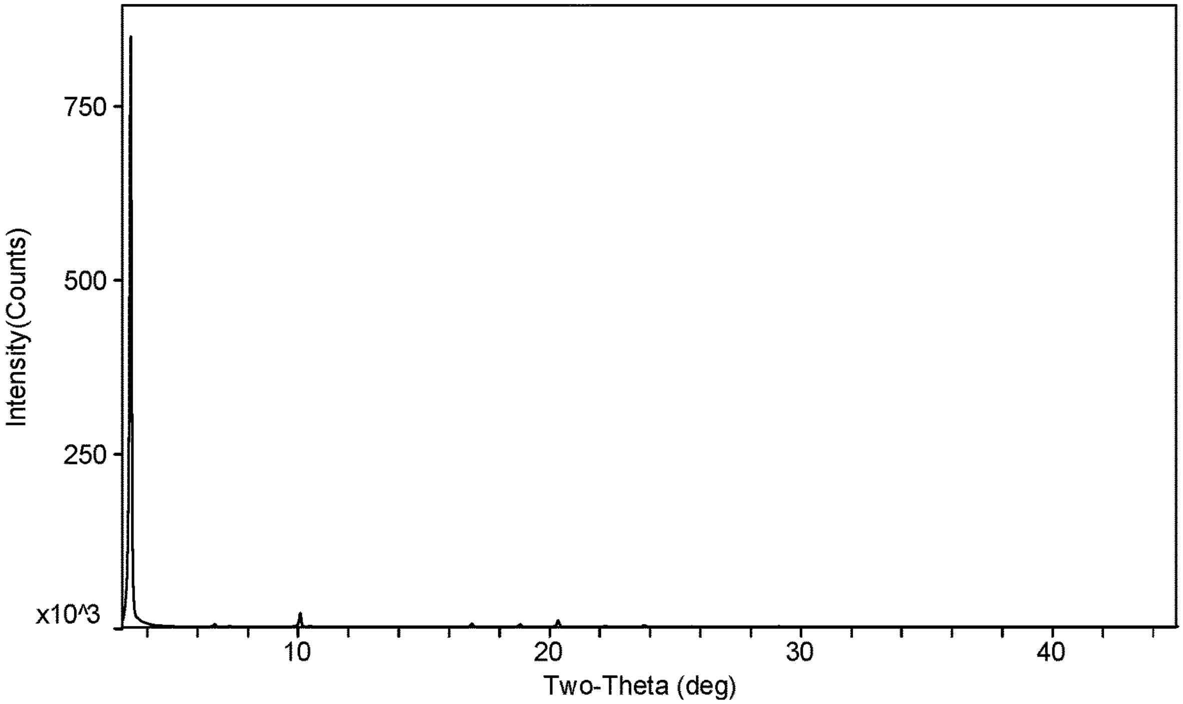
FIG. 11 is an XRPD pattern of the crystalline form D of Fingolimod embonate obtained in Example 7.

The XRPD pattern of the crystalline form D of Fingolimod embonate is shown in FIG. 11.

The XRPD analysis of the crystalline form D of Fingolimod embonate is shown in Table 6:

TABLE 6

| 2θ/° | Relative intensity I/% |
|---|---|
| 3.349 | 100 |
| 4.994 | 0.2 |
| 6.673 | 0.4 |
| 7.279 | 0.1 |
| 8.862 | 0 |
| 10.101 | 2.3 |
| 10.48 | 0.1 |
| 13.087 | 0 |
| 13.497 | 0 |
| 13.778 | 0.1 |
| 15.453 | 0 |
| 16.226 | 0 |
| 16.896 | 0.5 |
| 17.385 | 0 |
| 17.84 | 0 |
| 18.828 | 0.4 |
| 19.471 | 0 |
| 20.325 | 1 |
| 22.223 | 0.1 |
| 23.762 | 0.3 |
| 25.654 | 0.1 |
| 27.372 | 0 |
| 29.109 | 0.1 |

Example 8: Preparation of Crystalline Form E of Fingolimod Embonate 25 mg of a sample of the crystalline form B of Fingolimod embonate prepared in Example 3 was taken, and 0.2 mL of 1,4-dioxane was added. The resulting mixture was volatilized at 60° C. to give the crystalline form E of Fingolimod embonate.

Figure 12:
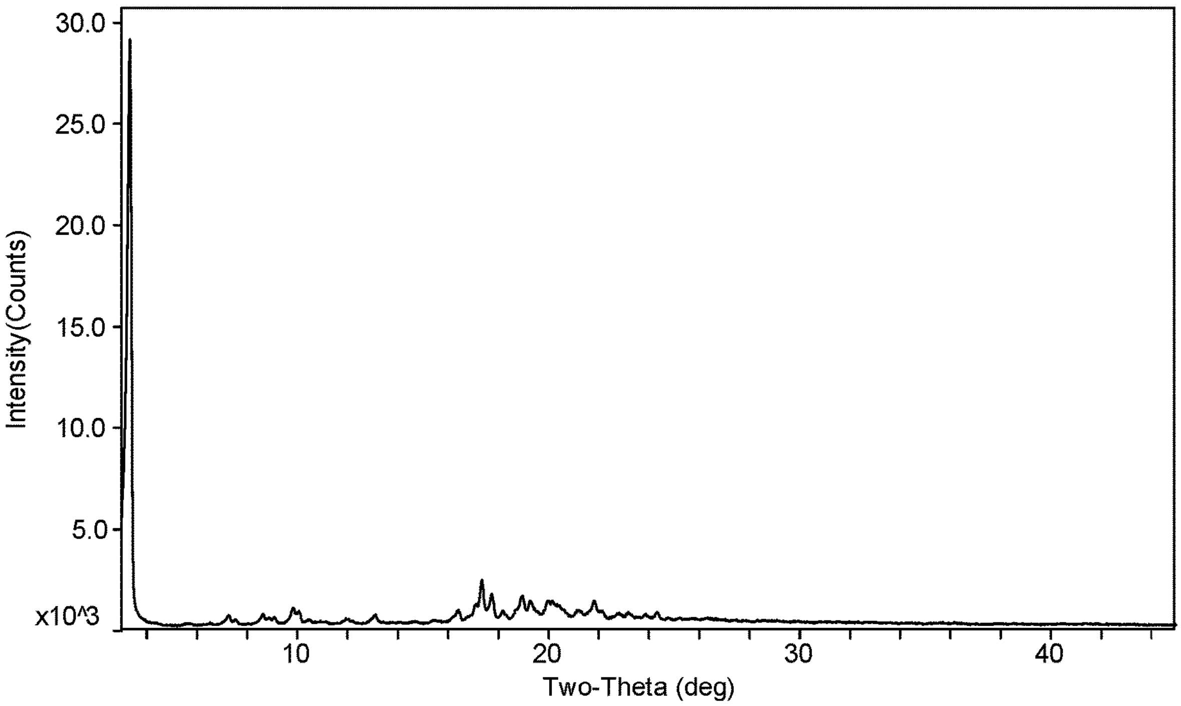
FIG. 12 is an XRPD pattern of the crystalline form E of Fingolimod embonate obtained in Example 8.

The XRPD pattern of the crystalline form E of Fingolimod embonate is shown in FIG. 12.

The XRPD analysis of the crystalline form E of Fingolimod embonate is shown in Table 7:

TABLE 7

| 2θ/° | Relative intensity I/% |
|---|---|
| 3.334 | 100 |
| 7.263 | 1.6 |
| 7.502 | 0.8 |
| 8.624 | 1.6 |
| 8.878 | 0.9 |
| 9.078 | 1 |
| 9.848 | 2.5 |
| 10.083 | 1.9 |
| 10.459 | 0.6 |
| 11.941 | 0.9 |
| 13.121 | 1.4 |
| 16.416 | 1.7 |
| 17.073 | 2.3 |
| 17.346 | 6.5 |
| 17.741 | 4.1 |
| 18.16 | 1.2 |
| 18.963 | 3.5 |
| 19.261 | 2.5 |
| 19.972 | 2.3 |
| 21.215 | 0.9 |
| 21.826 | 2.9 |
| 22.832 | 0.8 |
| 23.185 | 1 |
| 23.877 | 0.6 |
| 24.333 | 1 |

Example 9: Preparation of Crystalline Form F of Fingolimod Embonate 30 mg of a sample of the crystalline form B of Fingolimod embonate prepared in Example 3 was taken, and 0.5 mL of n-heptane and 0.5 mL of isopropyl acetate were added to form a slurry. The resulting mixture was stirred at 60° C. for 7 days to give a crystalline form F of Fingolimod embonate.

Figure 13:
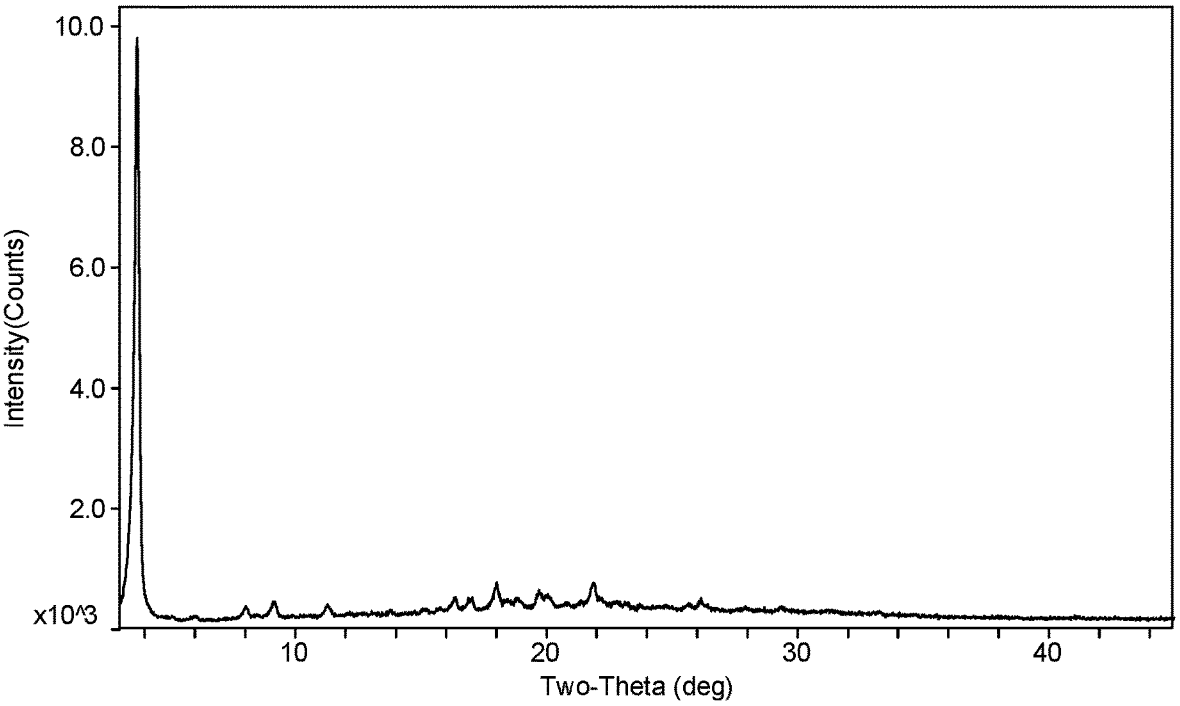
FIG. 13 is an XRPD pattern of the crystalline form F of Fingolimod embonate obtained in Example 9.

The XRPD pattern of the crystalline form F of Fingolimod embonate is shown in FIG. 13.

The XRPD analysis of the crystalline form F of Fingolimod embonate is shown in Table 8:

TABLE 8

| 2θ/° | Relative intensity I/% |
|---|---|
| 3.709 | 100 |
| 8.03 | 1.8 |
| 9.176 | 2.6 |
| 11.307 | 1.9 |
| 16.379 | 2.1 |
| 17.046 | 2.1 |
| 18.016 | 3.7 |
| 18.829 | 1.2 |
| 19.696 | 2.8 |
| 20.05 | 2.1 |
| 21.885 | 3.9 |

Example 10: Preparation of Crystalline Form G of Fingolimod Embonate 30 mg of a sample of the crystalline form B of Fingolimod embonate prepared in Example 3 was taken, and 0.1 mL of N,N-dimethylformamide and 1 mL of water were added to form a slurry. The slurry was stirred at 60° C. for 7 d to give the crystalline form G of Fingolimod embonate.

Figure 14:
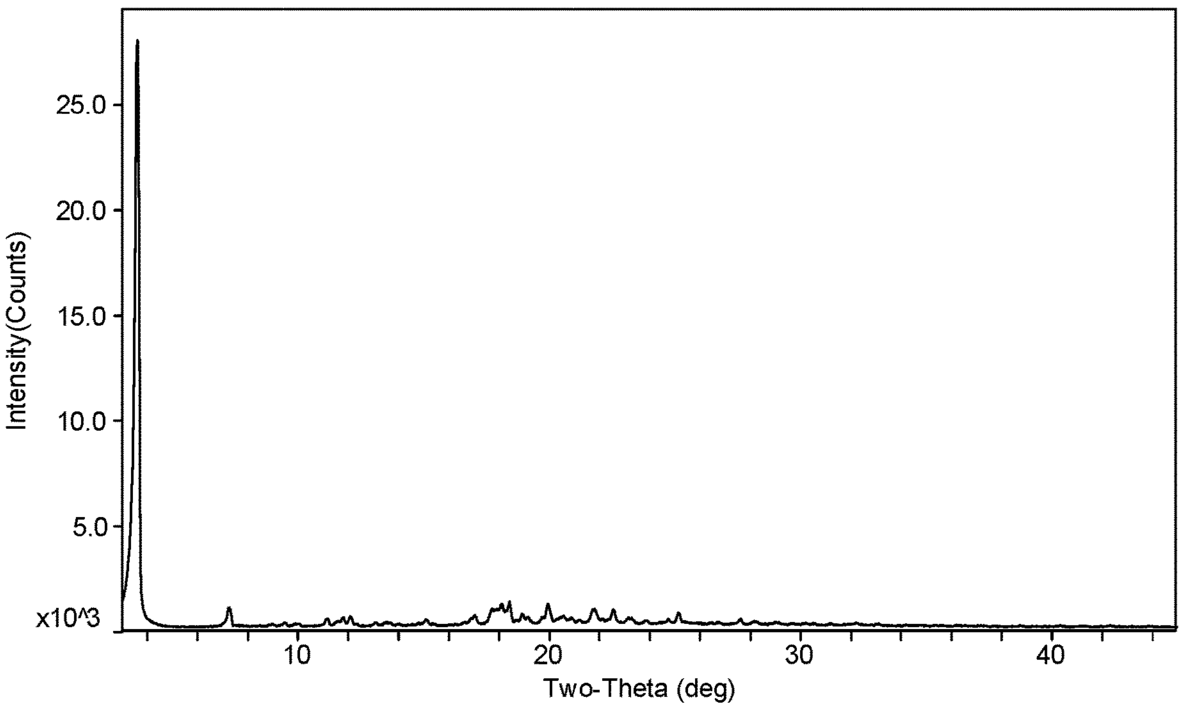
FIG. 14 is an XRPD pattern of the crystalline form G of Fingolimod embonate obtained in Example 10.

The XRPD pattern of the crystalline form G of Fingolimod embonate is shown in FIG. 14.

The XRPD analysis of the crystalline form G of Fingolimod embonate is shown in Table 9:

TABLE 9

| 2θ/° | Relative intensity I/% |
|---|---|
| 3.611 | 100 |
| 7.243 | 3.2 |
| 8.965 | 0.4 |
| 9.454 | 0.6 |
| 10.027 | 0.4 |
| 11.203 | 1 |
| 11.568 | 0.8 |
| 11.802 | 1.4 |
| 12.081 | 1.5 |
| 13.135 | 0.5 |
| 13.522 | 0.7 |
| 15.097 | 1 |
| 17.03 | 1.5 |
| 18.096 | 3.1 |
| 18.412 | 3.6 |
| 18.926 | 1.3 |
| 19.143 | 0.9 |
| 19.933 | 3 |
| 20.543 | 1.2 |
| 20.861 | 0.6 |
| 21.806 | 2.2 |
| 22.557 | 2.2 |
| 23.186 | 0.9 |
| 23.913 | 0.5 |
| 24.732 | 0.7 |
| 25.143 | 1.9 |
| 27.624 | 0.8 |
| 28.141 | 0.5 |

Example 11: Preparation of Crystalline Form H of Fingolimod Embonate 100 mg of a sample of the crystalline form B of Fingolimod embonate prepared in Example 3 was taken, and 0.5 mL of ethanol was added for complete dissolution before 1 mL of water was added slowly. The resulting mixture was stirred for crystallization to give the crystalline form H of Fingolimod embonate.

Figure 15:
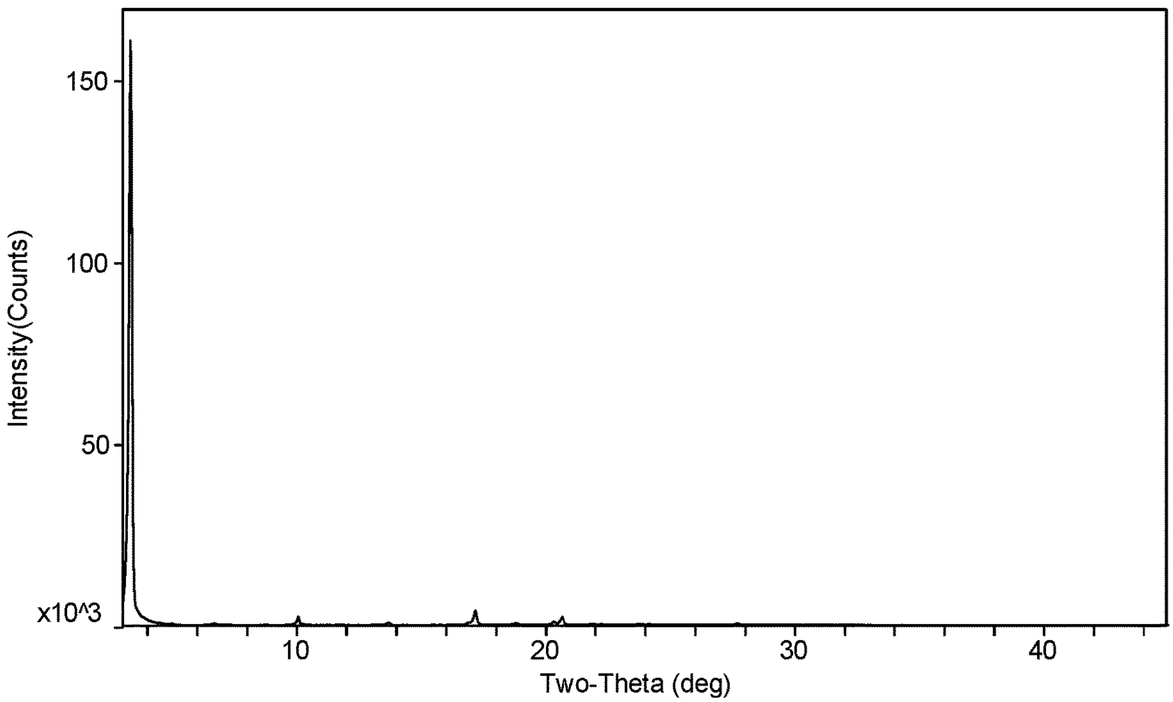
FIG. 15 is an XRPD pattern of the crystalline form H of Fingolimod embonate obtained in Example 11.

The XRPD pattern of the crystalline form H of Fingolimod embonate is shown in FIG. 15.

The XRPD analysis of the crystalline form H of Fingolimod embonate is shown in Table 10:

TABLE 10

| 2θ/° | Relative intensity I/% |
|---|---|
| 3.317 | 100 |
| 4.973 | 0.3 |
| 6.688 | 0.3 |
| 7.255 | 0.1 |
| 10.065 | 1.4 |
| 13.695 | 0.4 |
| 17.167 | 2.4 |
| 18.788 | 0.3 |
| 20.29 | 0.5 |
| 20.644 | 1.3 |
| 21.827 | 0.1 |
| 22.217 | 0.1 |
| 23.725 | 0.1 |
| 27.686 | 0.3 |

Example 12: Preparation of Fingolimod Free Base 12.6 g of Fingolimod hydrochloride was taken, and 480 mL of water was added. The mixture was stirred for complete dissolution. Then aqueous ammonia was added slowly dropwise and the pH was adjusted to 9-10. The mixture was stirred for another 1 h and filtered, and the filtrate was dried in vacuum at room temperature for 3 h to give 11.1 g of Fingolimod free base.

Example 13: Preparation of Crystalline Form K of Fingolimod Embonate 1000 mg of the Fingolimod free base prepared in Example 12 was taken, and 50 mL of n-butyl acetate was added. The mixture was stirred at 60° C. for complete dissolution. Then 530 mg of embonic acid was added. The resulting mixture was stirred for reaction for 4 h, cooled to room temperature, stirred overnight, filtered, and dried in vacuum overnight at 40° C. to give the crystalline form K of Fingolimod embonate.

Figure 16:
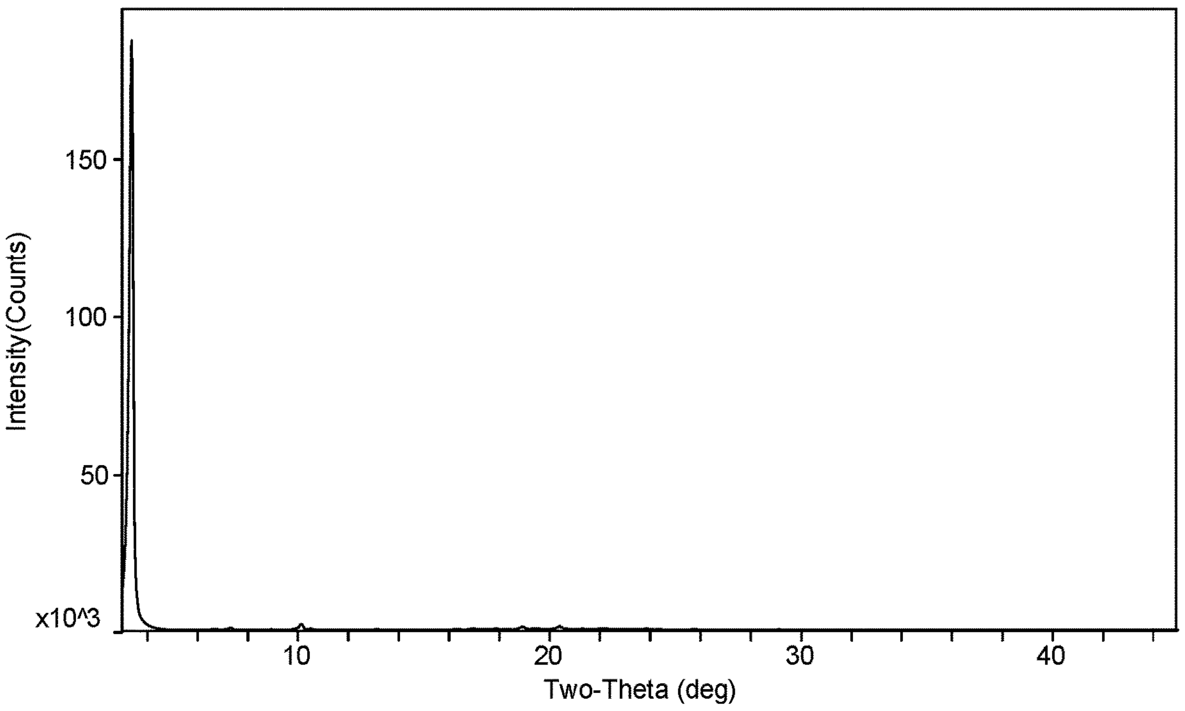
FIG. 16 is an XRPD pattern of the crystalline form K of Fingolimod embonate obtained in Example 13.

The XRPD pattern of the crystalline form K of Fingolimod embonate is shown in FIG. 16.

The XRPD analysis of the crystalline form K of Fingolimod embonate is shown in Table 11:

TABLE 11

| 2θ/° | Relative intensity I/% |
|---|---|
| 3.393 | 100 |
| 6.693 | 0.2 |
| 7.284 | 0.4 |
| 10.161 | 1 |
| 10.501 | 0.2 |
| 13.142 | 0.1 |
| 13.798 | 0.1 |
| 16.279 | 0.1 |
| 16.989 | 0.2 |
| 17.425 | 0.1 |
| 17.858 | 0.1 |
| 18.219 | 0.1 |
| 18.942 | 0.4 |
| 20.403 | 0.5 |

Example 14: Preparation of Crystalline Form 1 of Fingolimod 1-Hydroxy-2-Naphthoate Step 1: 5500 mg of 1-hydroxy-2-naphthoic acid was taken, and 75 mL of ethyl acetate was added. The resulting mixture was stirred in a water bath at 60° C. for dissolution and filtered. The filtrate was collected.

Step 2: 7230 mg of Fingolimod free base from Example 12 was taken, and 250 mL of ethyl acetate was added. The resulting mixture was incubated in a water bath at 60° C. for dissolution.

Step 3: A 1-hydroxy-2-naphthoic acid solution was added slowly and dropwise at 60° C. under stirring to a Fingolimod solution, before 17 mL of ethyl acetate was added for washing. The resulting mixture was stirred overnight at room temperature and filtered. The filter cake was washed with 85 mL of ethyl acetate, and dried in vacuum overnight at 35° C. to give Fingolimod 1-hydroxy-2-naphthoate, which was confirmed by XRPD to be the crystalline form 1 of Fingolimod 1-hydroxy-2-naphthoate.

Figure 17:
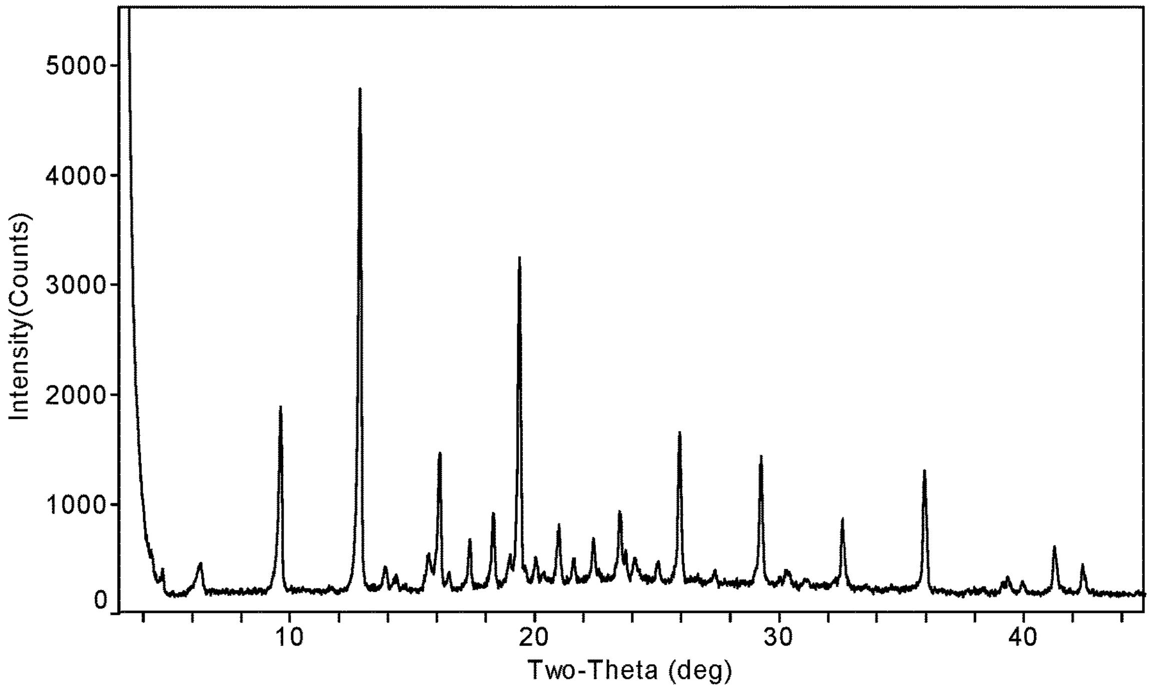
FIG. 17 is an XRPD pattern of the crystalline form 1 of Fingolimod 1-hydroxy 2-naphthoate obtained in Example 14.

The XRPD pattern of the crystalline form 1 of Fingolimod 1-hydroxy-2-naphthoate is shown in FIG. 17;

The XRPD analysis of the crystalline form 1 of Fingolimod 1-hydroxy-2-naphthoate is shown in Table 12:

TABLE 12

| 2θ/° | Relative intensity I/% |
|---|---|
| 3.198 | 100 |
| 6.352 | 0.1 |
| 9.631 | 0.8 |
| 12.867 | 2.1 |
| 13.876 | 0.1 |
| 14.351 | 0.1 |
| 15.687 | 0.1 |
| 16.121 | 0.6 |
| 16.513 | 0.1 |
| 17.362 | 0.2 |
| 18.298 | 0.3 |
| 19.378 | 1.4 |
| 20.034 | 0.1 |
| 21.015 | 0.2 |
| 21.612 | 0.1 |
| 22.419 | 0.2 |
| 23.486 | 0.3 |
| 24.115 | 0.1 |
| 25.092 | 0.1 |
| 25.948 | 0.6 |
| 29.263 | 0.5 |
| 30.311 | 0.1 |
| 32.599 | 0.3 |
| 35.955 | 0.5 |

Figure 18:
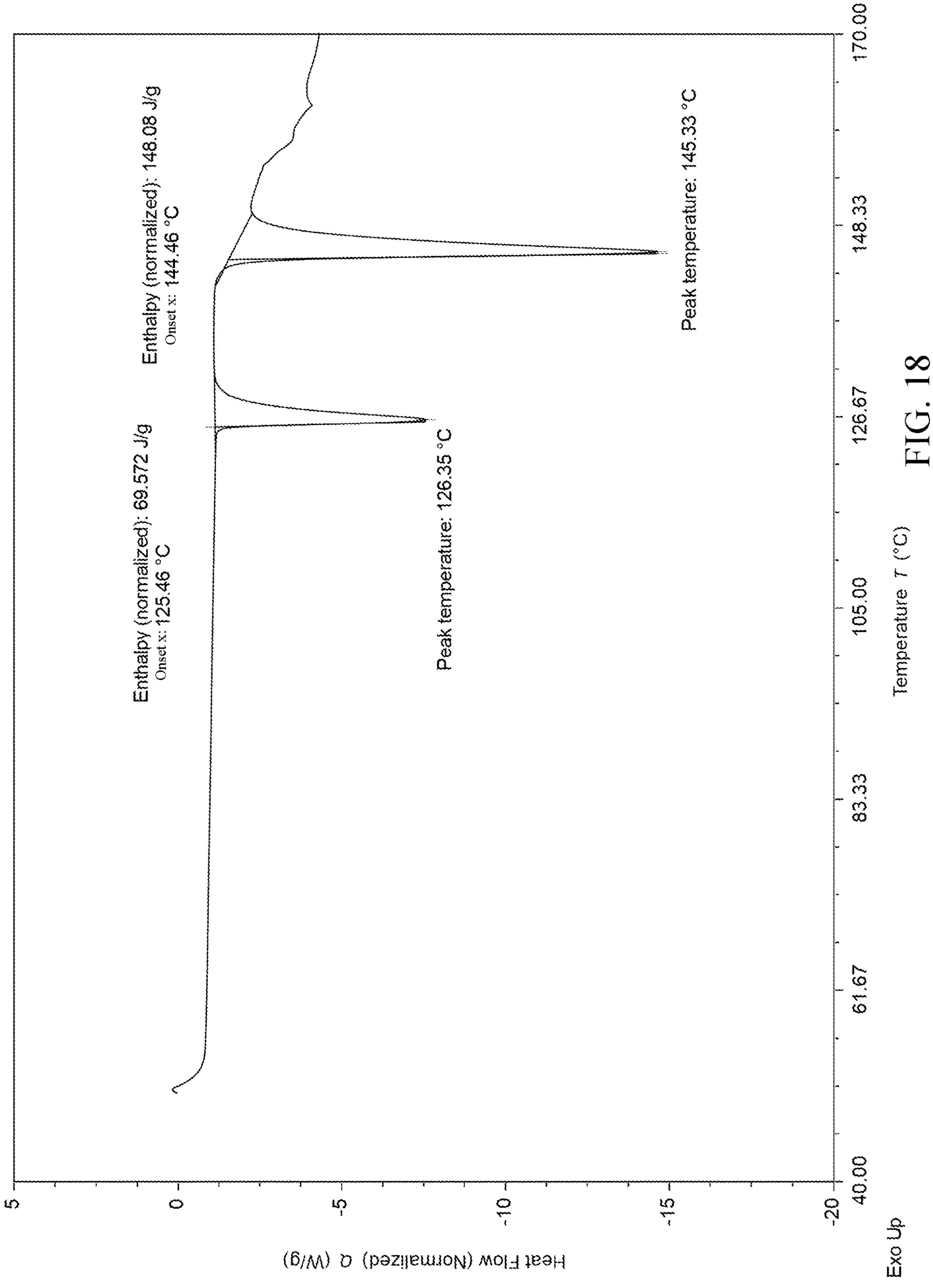
FIG. 18 is a DSC pattern of the crystalline form 1 of Fingolimod 1-hydroxy 2-naphthoate obtained in Example 14.
Figure 19:
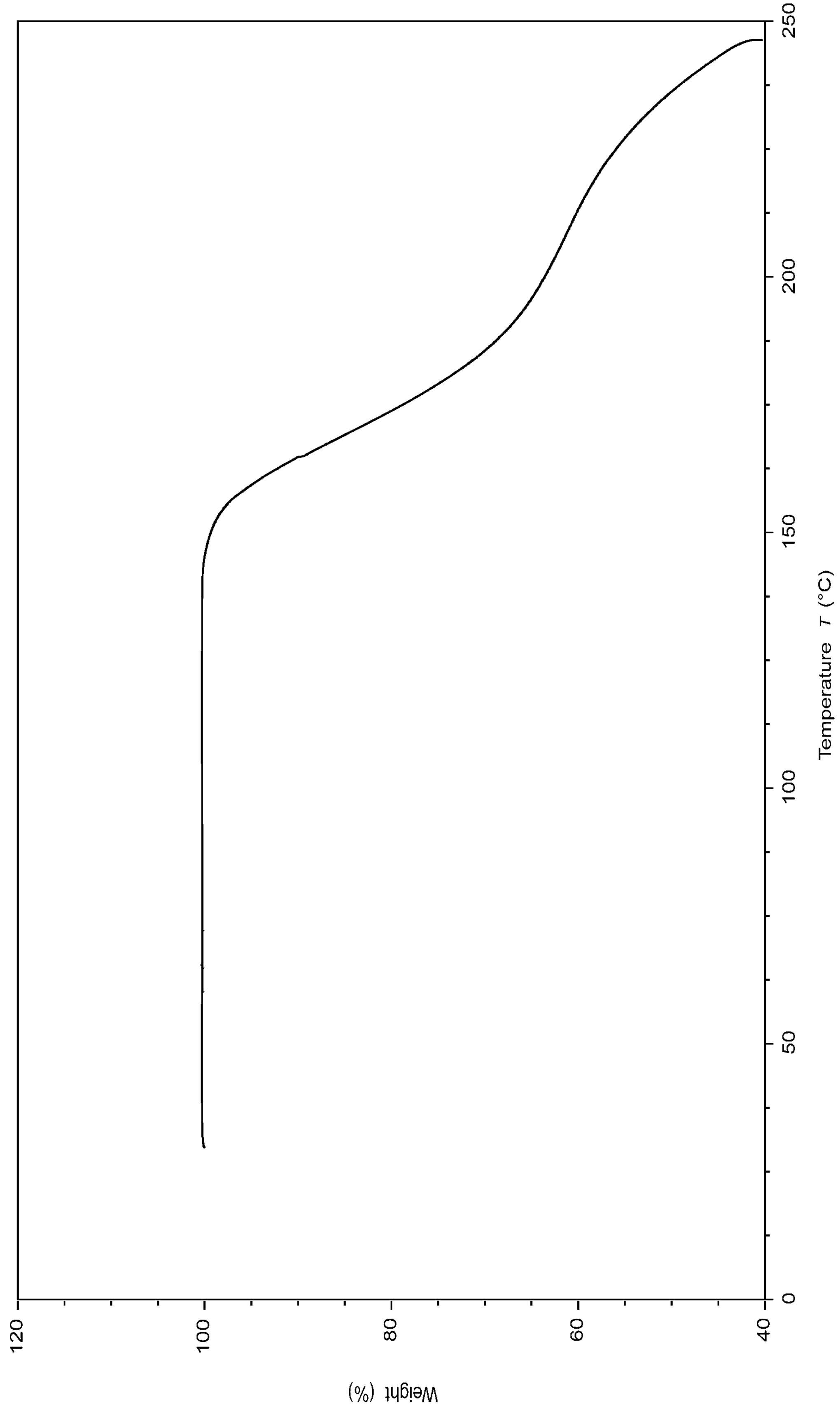
FIG. 19 is a TGA pattern of the crystalline form 1 of Fingolimod 1-hydroxy 2-naphthoate obtained in Example 14.
Figure 20:
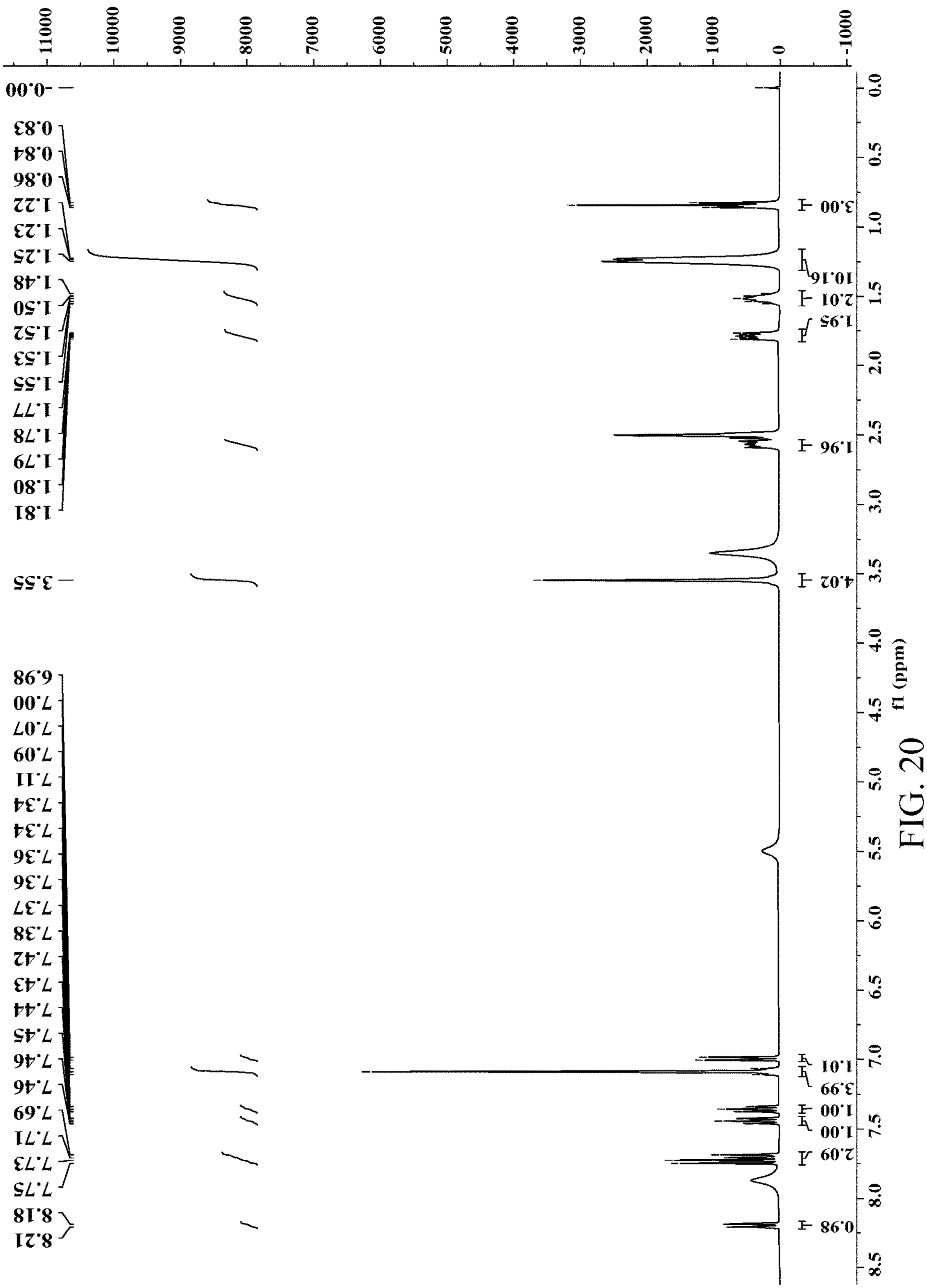
FIG. 20 is a $^1$H-NMR spectrum of the crystalline form 1 of Fingolimod 1-hydroxy 2-naphthoate obtained in Example 14.

A DSC pattern of the crystalline form 1 of Fingolimod 1-hydroxy-2-naphthoate is shown in FIG. 18;

A TGA pattern of the crystalline form 1 of Fingolimod 1-hydroxy-2-naphthoate is shown in FIG. 19;

A $^1$H-NMR spectrum of the crystalline form 1 of Fingolimod 1-hydroxy-2-naphthoate is shown in FIG. 20, indicating that Fingolimod and 1-hydroxy-2-naphthoic acid formed the salt in a ratio of 1:1.

Example 15: Preparation of Formulation of Crystalline Form 1 of Fingolimod 1-Hydroxy-2-Naphthoate

TABLE 13

| | Amount (mg) | | |
|---|---|---|---|
| Component | Formula 1 | Formula 2 | Formula 3 |
| Crystalline form 1 of Fingolimod 1-hydroxy-2-naphthoate | 242.3 | 242.3 | 242.3 |
| Poloxamer 188 | 10 | 10 | 10 |
| Sodium carboxymethylcellulose | / | 100 | / |
| Polyethylene glycol 4000 | / | / | 750 |
| Disodium hydrogen phosphate | 45 | 45 | 45 |
| Sodium dihydrogen phosphate | 9 | 9 | 9 |
| Water for injection | | Qs10 mL | |

Preparation Process:

(1) The formulation amounts of poloxamer 188, sodium carboxymethylcellulose, polyethylene glycol 4000, disodium hydrogen phosphate, and sodium dihydrogen phosphate as shown in Table 13 were taken, and added to water for injection that was about 60% of the total amount of the preparation. The mixture was stirred for dissolution and dispersion;

(2) The formulation amount of the crystalline form 1 of Fingolimod 1-hydroxy-2-naphthoate that was sieved through a 400-mesh sieve, as shown in Table 13, was added, and fully wetted and dispersed;

(3) The resulting mixture was diluted with water for injection to 10 mL, and shaken well to give a suspension of the crystalline form 1 of Fingolimod 1-hydroxy-2-naphthoate.

Syringeability and settling ratio examinations on samples prepared according to formulas 1-3 demonstrated that the sample of formula 2 has a good syringeability and settling ratio.

Example 16: Preparation of Formulation of Crystalline Form 1 of Fingolimod 1-Hydroxy-2-Naphthoate As shown in Table 14, the amounts of polyethylene glycol 4000 used in formula 3 of Example 15 were adjusted to 200 mg, 300 mg, 400 mg, 500 mg, and 600 mg to give formulas 4, 5, 6, 7, and 8, respectively. Syringeability and settling ratio examinations on samples prepared according to formulas 4-8 demonstrated good syringeabilities and settling ratios.

TABLE 14

| | Amount (mg) | | | | |
|---|---|---|---|---|---|
| Component | Formula 4 | Formula 5 | Formula 6 | Formula 7 | Formula 8 |
| Crystalline form 1 of Fingolimod 1-hydroxy-2-naphthoate | 242.3 | 242.3 | 242.3 | 242.3 | 242.3 |
| Poloxamer 188 | 10 | 10 | 10 | 10 | 10 |
| Polyethylene glycol 4000 | 200 | 300 | 400 | 500 | 600 |
| Disodium hydrogen phosphate | 45 | 45 | 45 | 45 | 45 |
| Sodium dihydrogen phosphate | 9 | 9 | 9 | 9 | 9 |
| Water for injection | | | Qs10 mL | | |

Example 17: Preparation of Oral Formulation Sample of Fingolimod Hydrochloride 3.676 mg of Fingolimod hydrochloride was taken, and dissolved and diluted with water for injection to 100 mL to give an oral formulation sample of Fingolimod hydrochloride.

Example 18: Preparation of formulation sample of crystalline form 1 of Fingolimod 1-hydroxy-2-naphthoate (1) 10 mg of poloxamer 188, 750 mg of polyethylene glycol 4000, 45 mg of disodium hydrogen phosphate, and 9 mg of sodium dihydrogen phosphate were taken and added to about 6 mL of water for injection. The mixture was stirred for dissolution and dispersion;

(2) 242.3 mg of the crystalline form 1 of Fingolimod 1-hydroxy-2-naphthoate sieved through a 400-mesh sieve was added, and fully wetted and dispersed;

(3) The resulting mixture was diluted with water for injection to 10 mL, and shaken well to give a suspension formulation sample of the crystalline form 1 of Fingolimod 1-hydroxy-2-naphthoate.

Example 19: Comparison of Solid State Stability

The crystalline form 1 of Fingolimod 1-hydroxy-2-naphthoate prepared in Example 14, the crystalline form A of Fingolimod embonate prepared in Example 3, and Fingolimod hydrochloride were stood in a high temperature (60° C.)condition, a high humidity (25° C./90% RH) condition, an accelerated (40° C./75% RH) condition, an illumination ($1.2\times 10^6$ Lux·hr) condition, and a long-term (25° C./60% RH) condition, and samples were taken on day 0, day 5, and day 10 for related substance detection by HPLC.

The results for related substances are shown in Table 15, indicating that the crystalline form 1 of Fingolimod 1-hydroxy-2-naphthoate of the present disclosure is relatively stable—the total related substances remained substantially unchanged when the samples were stood in the above conditions for 10 d, while the crystalline form A of Fingolimod embonate was relatively stable in other conditions than the illumination condition where the impurities were slightly increased.

TABLE 15

| Results for related substances | | | | | | | |
|---|---|---|---|---|---|---|---|
| Sample | | | Changes in total related substances relative to day 0 (%) | | | | |
| Component | Example No. | Time | High temperature | High humidity | Illumination | Accelerated | Long-term |
| Fingolimod hydrochloride | / | Day 0 | | | 0 | | |
| | | Day 5 | 0.03 | −0.07 | −0.04 | −0.07 | 0.04 |
| | | Day 10 | 0.02 | −0.07 | −0.03 | 0.01 | −0.12 |
| Crystalline form 1 of Fingolimod 1-hydroxy-2-naphthoate | Example 14 | Day 0 | | | 0 | | |
| | | Day 5 | −0.05 | −0.04 | −0.05 | −0.09 | −0.17 |
| | | Day 10 | −0.16 | −0.07 | 0.02 | −0.07 | −0.15 |
| Crystalline form A of Fingolimod embonate | Example 3 | Day 0 | | | 0 | | |
| | | Day 5 | −0.04 | 0.12 | 0.2 | 0 | 0.08 |
| | | Day 10 | −0.21 | 0.11 | 0.3 | −0.11 | −0.01 |

Example 20: Comparison of Solubility

The crystalline form 1 of Fingolimod 1-hydroxy-2-naphthoate prepared in Example 14, the crystalline form B of Fingolimod embonate prepared in Example 2, Fingolimod hydrochloride and the Fingolimod free base prepared in Example 12 were added to corresponding media described below. The mixtures were shaken at 37° C. for 24 h and filtered through 0.45 μm aqueous-phase filter membranes. The filtrates were collected for determination of solubility by high-performance liquid chromatography. The corresponding media were acetate buffer solutions at pH 3 and pH 5 and phosphate buffer solutions at pH 7 and pH 9, and the water was ultrapure water.

The results are shown in Table 16, indicating that the solubilities of Fingolimod free base and Fingolimod hydrochloride were greatly different in the media, and that Fingolimod hydrochloride dissociated into the Fingolimod free base in media having high pH values. However, the solubilities of the Fingolimod 1-hydroxy-2-naphthoate, embonate, and crystalline forms thereof prepared in the present disclosure were greatly reduced in water and low-pH (pH is not more than 5) conditions, the solubility of Fingolimod 1-hydroxy-2-naphthoate in water was 5.46 μg/mL, which is equivalent to one fourth to one fifth of the solubility of Fingolimod free base (about 23 μg/mL), and one thousandth to one twenty-six hundredth of the solubility of Fingolimod hydrochloride (about 14 mg/mL), and the solubilities were all relatively low in media having different pH values, that is, as the Fingolimod 1-hydroxy-2-naphthoate, embonate, and crystalline forms thereof have sustained-release effects, their equivalent solubilities in media having different pH values enable the minimized dependence of release on pH. As such, the influence of pH in environments of different pH in the body on their release rates and burst releases or excessive plasma concentrations in local areas in the body are avoided, and the difference in drug release between individuals is reduced. In addition, the Fingolimod 1-hydroxy-2-naphthoate, embonate, and crystalline forms thereof are suitable for use in long-acting preparations and allow fewer doses and thus improved patient compliance, thereby having a good commercial prospect.

TABLE 16

Results for solubility

| Sample | | Solubility (μg/mL) | | | | |
|---|---|---|---|---|---|---|
| Component | Example No. | pH 3 | pH 5 | Water | pH 7 | pH 9 |
| Fingolimod free base | Example 12 | 5561.36 | 473.53 | 23.39 | <0.15 | <0.15 |
| Fingolimod hydrochloride | / | >33500 | >15600 | >13900 | <0.15 | <0.15 |
| Crystalline form 1 of Fingolimod 1-hydroxy-2-naphthoate | Example 14 | 20.07 | 9.17 | 5.46 | 0.54 | 0.58 |
| Crystalline form B of Fingolimod embonate | Example 2 | 36.18 | 1.75 | 0.2 | 21.26 | 5.8 |

Example 21: Stability Comparison of Formulas

Samples of formula 3 prepared in Example 15 were taken and stood in a high temperature (60° C.) condition, an accelerated (40° C./75% RH) condition, and a long-term (25° C./60% RH) condition, and samples were taken on day 0, day 5, and day 10 for HPLC analysis.

The results are shown in Table 17, indicating that the formulation samples prepared in the present disclosure are relatively stable in such conditions, and the total related substances have no significant changes after standing for 10 days.

TABLE 17

Results for stability

| | | Changes in total related substances relative to day 0 (%) | | |
|---|---|---|---|---|
| Name | Time | High temperature | Accelerated | Long-term |
| Suspension | Day 0 | | 0 | |
| | Day 5 | 0.09 | 0 | 0.05 |
| | Day 10 | 0.33 | 0.08 | 0.15 |

The samples of the formulas prepared in Example 18 exhibited the same stabilities as those in Example 15.

Example 21: Pharmacokinetic Study

Six male SD rats were divided into two groups. One group was given a single intramuscular dose of 3 mg/kg of the sample of the crystalline form of Fingolimod 1-hydroxy-2-naphthoate (Example 18), and plasma was collected at 0, 1 h, 3 h, 7 h, 24 h, 4 d, 7 d, 11 d, 15 d, 20 d, 25 d, 30 d, and 35 d post-dose; the other group was given a single oral dose of 0.1 mg/kg of the sample of Fingolimod hydrochloride (Example 17), and plasma was collected at 5 min, 15 min, 30 min, 1 h, 2 h, 3 h, 4 h, 6 h, 8 h, 12 h and 24 h post-dose. In the whole study, the animals in the intramuscular injection group were given ad libitum access to food and water, and those in the oral group were fasted overnight before administration and given access to food at 4 h post-dose.

Collection of plasma sample: about 150 μL of blood was collected from the jugular vein (whole blood was centrifuged within 30 min to isolate plasma) and placed in a tube containing anticoagulant EDTA-K2, and after treatment, plasma was stored in a freezer at −70° C. before use.

Figure 21:
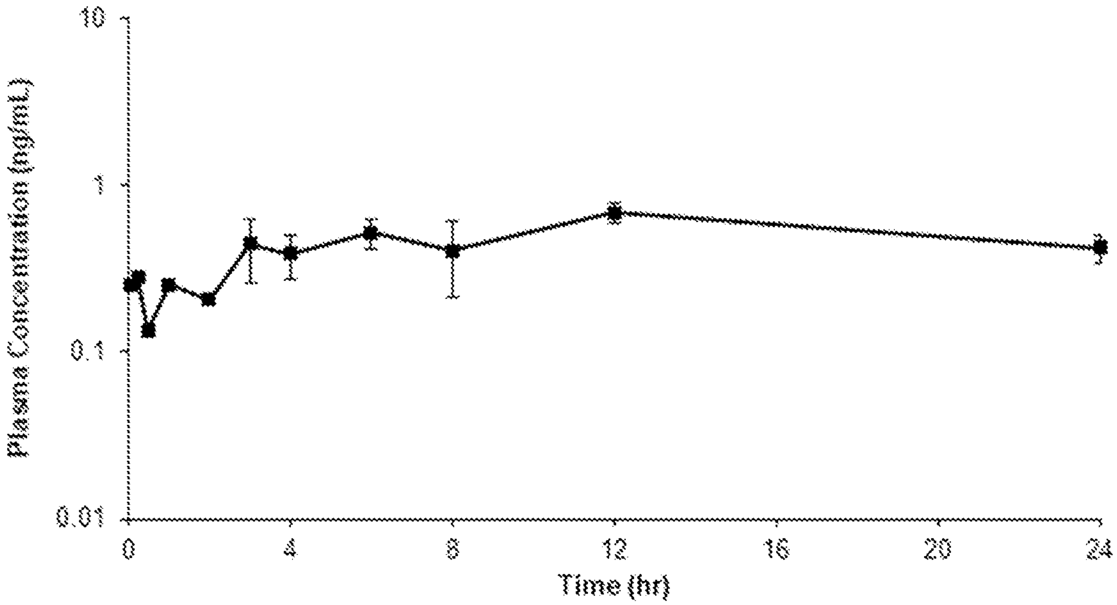
FIG. 21 is a graph showing the relationship between mean plasma concentration and time for the oral formulation sample in Example 21.
Figure 22:
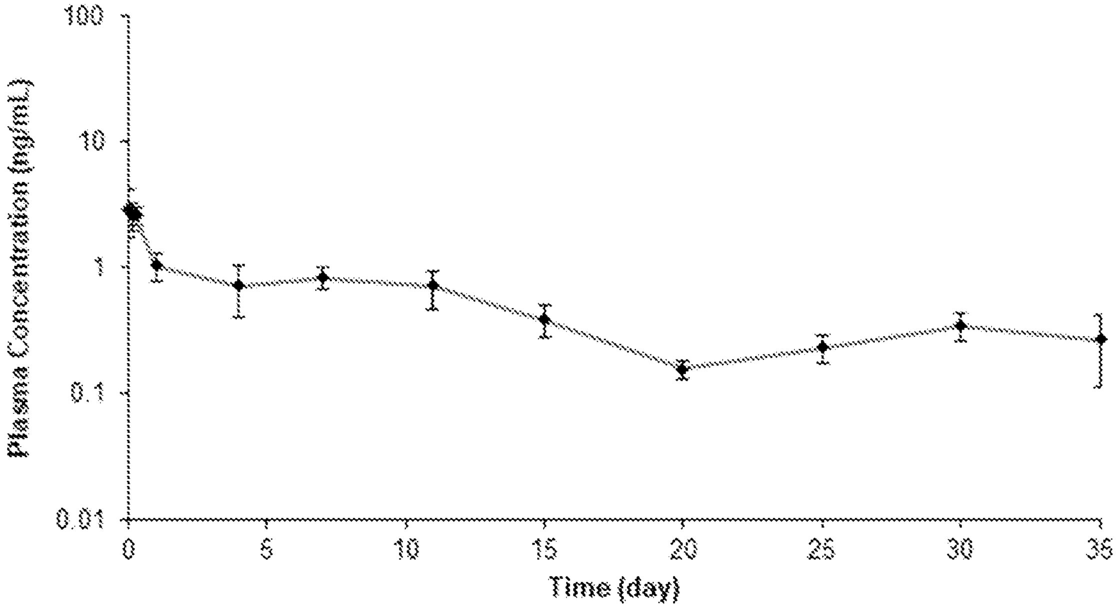
FIG. 22 is a graph showing the relationship between mean plasma concentration and time for the suspension formulation sample in Example 21.

Pretreatment of plasma sample: to 30 μL of plasma sample, 200 μL of internal standard solution (40 ng/mL Glipizide acetonitrile solution) was added; the mixture was vortexed for 1 min and centrifuged at 5800 rpm at 4° C. for 10 min; 100 μL of supernatant was transferred to a new plate 5 μL of the solution was taken for LC-MS/MS. The pharmacokinetics of Fingolimod in animals are shown in Table 18 and Table 19, and the drug concentration-time curves are shown in FIG. 21 and FIG. 22.

The results show that the plasma concentration of the Fingolimod oral group reached the peak value at 12 h post-dose; the plasma concentration could be maintained above 0.3 ng/ml within 24 h, and the MRT was only 12 h. The plasma concentration of the Fingolimod 1-hydroxy-2-naphthoate injection group reached the peak value at 3 h post-dose. The plasma concentration could reach a relatively steady state within 1 day, the plasma concentration was maintained above 0.3 ng/ml for at least 15 days, and the MRT was 12 days, indicating that the preparation takes effect quickly and has a long sustained release period; Cmax did not increase in proportion to the dose, and was far from the toxic concentration, indicating relatively high safety.

TABLE 18

Pharmacokinetics in intramuscular injection group

| PK parameters | Unit | Rat#1 | Rat#2 | Rat#3 | Mean | SD | CV(%) |
|---|---|---|---|---|---|---|---|
| $T_{max}$ | day | 0.0420 | 0.0420 | 0.292 | 0.125 | 0.144 | 115 |
| $C_{max}$ | ng/mL | 4.36 | 2.45 | 2.93 | 3.25 | 0.994 | 30.6 |
| $T_{1/2}$ | day | 9.75 | 11.8 | 17.5 | 13.0 | 4.00 | 30.7 |
| $AUC_{last}$ | day * ng/mL | 19.8 | 14.9 | 17.7 | 17.5 | 2.46 | 14.0 |
| $AUC_{INF}$ | day * ng/mL | 23.9 | 16.7 | 28.1 | 22.9 | 5.80 | 25.3 |
| $MRT_{INF}$ | day | 17.3 | 17.4 | 29.7 | 21.5 | 7.12 | 33.2 |
| $MRT_{last}$ | day | 10.8 | 13.4 | 11.8 | 12.0 | 1.30 | 10.8 |

TABLE 19

Pharmacokinetics in oral group

| PK parameters | Unit | Rat#4 | Rat#5 | Rat#6 | Mean | SD | CV(%) |
|---|---|---|---|---|---|---|---|
| $T_{max}$ | hr | 12.0 | 12.0 | 12.0 | 12.0 | 0.00 | 0.00 |
| $C_{max}$ | ng/mL | 0.564 | 0.728 | 0.728 | 0.673 | 0.0947 | 14.1 |
| $T_{1/2}$ | hr | NA | NA | NA | NA | NA | NA |
| $AUC_{last}$ | hr * ng/mL | 11.0 | 12.0 | 11.9 | 11.6 | 0.576 | 4.95 |
| $AUC_{INF}$ | hr * ng/mL | NA | NA | NA | NA | NA | NA |
| $MRT_{INF}$ | hr | NA | NA | NA | NA | NA | NA |
| $MRT_{last}$ | hr | 12.2 | 13.2 | 12.0 | 12.5 | 0.649 | 5.21 |

The invention claimed is:

1. A crystalline form of the salt of Fingolimod of formula I:

I

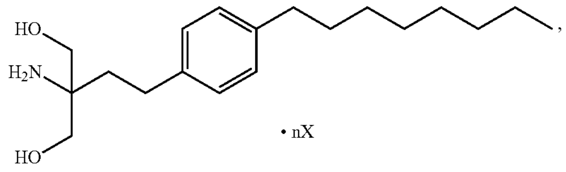

wherein X is embonic acid or 1-hydroxy-2-naphthoic;

the crystalline form is selected from crystalline forms of A, B, C, D, E, F, G, H, I, J and K of Fingolimod embonate and a crystalline form 1 of Fingolimod 1-hydroxy-2-naphthoate;

the crystalline form B of Fingolimod embonate has an X-ray powder diffraction pattern comprising characteristic peaks at 2θ of 3.3°±0.2°, 17.1°±0.2°, 18.7°±0.2°, 19.1°±0.2°, 21.8°±0.2°, and 23.4°±0.2°;

in the crystalline form B of Fingolimod embonate, the molar ratio of Fingolimod to embonic acid is 1:0.5;

the crystalline form A of Fingolimod embonate has an X-ray powder diffraction pattern comprising characteristic peaks at 2θ of 3.2°±0.2°, 9.6°±0.2°, 12.5°±0.2°, 18.5°±0.2°, 19.3°±0.2°, and 20.4°±0.2°;

the crystalline form A of Fingolimod embonate is an anhydrate or a channel hydrate;

in the crystalline form A of Fingolimod embonate, the molar ratio of Fingolimod to embonic acid is 1:0.5;

the crystalline form I of Fingolimod embonate has an X-ray powder diffraction pattern comprising characteristic peaks at 2θ of 3.0°±0.2°, 3.3°±0.2°, 5.6±0.2°, 5.9°±0.2°, 6.9°±0.2°, 8.9°±0.2°, 9.8°±0.2°, 15.0°±0.2°, 16.2°−0.2°, 18.0°±0.2°, 18.8°±0.2°, 19.1°±0.2°, 19.6°±0.2°, 19.9°±0.2°, 21.0°±0.2°, 21.8°±0.2°, and 25.2°±0.2°;

the crystalline form J of Fingolimod embonate has an X-ray powder diffraction pattern comprising characteristic peaks at 2θ of 3.2°±0.2°, 5.3°±0.2°, 10.1°±0.2°, 10.8°±0.2°, 18.1°±0.2°, 19.8°±0.2°, 20.6°±0.2°, and 21.7°±0.2°;

the crystalline form C of Fingolimod embonate has an X-ray powder diffraction pattern comprising characteristic peaks at 2θ of 3.2°±0.2°, 6.4°±0.2°, 9.6°±0.2°, 15.1°±0.2°, 19.8°±0.2°, and 20.4°±0.2°;

the crystalline form D of Fingolimod embonate has an X-ray powder diffraction pattern comprising characteristic peaks at 2θ of 3.3°±0.2°, 6.7°±0.2°, 10.1°±0.2°, 16.9°±0.2°, 18.8°±0.2°, and 20.3°±0.2°;

the crystalline form E of Fingolimod embonate has an X-ray powder diffraction pattern comprising characteristic peaks at 2θ of 3.3°±0.2°, 9.8°±0.2°, 17.3°±0.2°, 17.7°±0.2°, 19.0°±0.2°, and 21.8°±0.2°;

the crystalline form F of Fingolimod embonate has an X-ray powder diffraction pattern comprising characteristic peaks at 2θ of 3.7°±0.2°, 9.2°±0.2°, 16.4°±0.2°, 17.0°±0.2°, 18.0°±0.2°, 19.7°±0.2°, 20.1°±0.2°, and 21.9°±0.2°;

the crystalline form G of Fingolimod embonate has an X-ray powder diffraction pattern comprising characteristic peaks at 2θ of 3.6°±0.2°, 7.2°±0.2°, 18.1°±0.2°, 18.4°±0.2°, 19.9°±0.2°, 21.8°±0.2°, 22.6°±0.2°, and 25.1°±0.2°;

the crystalline form H of Fingolimod embonate has an X-ray powder diffraction pattern comprising characteristic peaks at 2θ of 3.3°±0.2°, 6.7°±0.2°, 10.1°–0.2°, 13.7°±0.2°, 17.2°±0.2°, 20.3°±0.2°, and 20.6°±0.2°;

the crystalline form K of Fingolimod embonate has an X-ray powder diffraction pattern comprising characteristic peaks at 2θ of 3.4°±0.2°, 6.7°±0.2°, 7.3°±0.2°, 10.2°±0.2°, 10.5°±0.2°, 17.0°±0.2°, 18.9°±0.2°, and 20.4°±0.2°;

the crystalline form 1 of Fingolimod 1-hydroxy-2-naphthoate has an X-ray powder diffraction pattern comprising characteristic peaks at 2θ of 3.2°±0.2°, 9.6°±0.2°, 12.9°±0.2°, 16.1°±0.2°, 19.4°±0.2°, and 25.9°±0.2°;

the crystalline form 1 of Fingolimod 1-hydroxy-2-naphthoate is an anhydrate; and in the crystalline form 1 of Fingolimod 1-hydroxy-2-naphthoate, the molar ratio of Fingolimod to 1-hydroxy-2-naphthoic acid is 1:1.

2. A pharmaceutical composition, comprising a therapeutically and/or prophylactically effective amount of the crystalline form of the salt of Fingolimod according to claim 1 and a pharmaceutically acceptable auxiliary material.

3. The pharmaceutical composition according to claim 2, wherein the pharmaceutical composition comprises a tablet, a capsule, a solution, a suspension, a long-acting injection, and a semisolid preparation.

4. A method for treating multiple sclerosis, comprising administering the pharmaceutical composition according to claim 2 to a subject in need thereof.

5. The crystalline form of the salt of Fingolimod according to claim 1, wherein:

the crystalline form B of Fingolimod embonate has an X-ray powder diffraction pattern comprising characteristic peaks at 2θ of 3.3°±0.2°, 17.1±0.2°, 17.7°±0.2°, 18.7°±0.2°, 19.1°±0.2°, 20.6°±0.2°, 21.8°±0.2°, and 23.4°±0.2°;

the crystalline form A of Fingolimod embonate has an X-ray powder diffraction pattern comprising characteristic peaks at 2θ of 3.2°±0.2°, 9.6°±0.2°, 12.5°±0.2°, 18.0°±0.2°, 18.5°±0.2°, 19.3°±0.2°, 20.4°±0.2°, and 24.3°±0.2°;

the crystalline form J of Fingolimod embonate has an X-ray powder diffraction pattern comprising characteristic peaks at 2θ of 3.2°±0.2°, 5.3°±0.2°, 6.3°±0.2°, 9.5°±0.2°, 10.1°±0.2°, 10.8°±0.2°, 13.5°±0.2°, 17.0°±0.2°, 17.8°±0.2°, 18.1°±0.2°, 19.8°±0.2°, 20.6°±0.2°, 21.7°±0.2°, 22.0°±0.2°, 24.5°±0.2°, and 25.5°±0.2°;

the crystalline form C of Fingolimod embonate has an X-ray powder diffraction pattern comprising characteristic peaks at 2θ of 3.2°±0.2°, 6.4°±0.2°, 9.6°±0.2°, 13.6°±0.2°, 15.1°±0.2°, 15.6°±0.2°, 19.8°±0.2°, and 20.4°±0.2°;

the crystalline form D of Fingolimod embonate has an X-ray powder diffraction pattern comprising characteristic peaks at 2θ of 3.3°±0.2°, 6.7°±0.2°, 7.2°±0.2°, 10.1°±0.2°, 16.9°±0.2°, 18.8°±0.2°, 20.3°±0.2°, and 23.8°±0.2°;

the crystalline form E of Fingolimod embonate has an X-ray powder diffraction pattern comprising characteristic peaks at 2θ of 3.3°±0.2°, 9.8°±0.2°, 17.3°±0.2°, 17.7°±0.2°, 19.0°±0.2°, 19.3°±0.2°, 20.0°±0.2°, and 21.8°±0.2°;

the crystalline form F of Fingolimod embonate has an X-ray powder diffraction pattern comprising characteristic peaks at 2θ of 3.7°±0.2°, 8.0±0.2°, 9.2°±0.2°, 11.3°±0.2°, 16.4°±0.2°, 17.0°±0.2°, 18.0°±0.2°, 18.8°±0.2°, 19.7°±0.2°, 20.1°±0.2°, and 21.9°±0.2°;

the crystalline form G of Fingolimod embonate has an X-ray powder diffraction pattern comprising characteristic peaks at 2θ of 3.6°±0.2°, 7.2°±0.2°, 9.0±0.2°, 9.5°±0.2°, 10.0°±0.2°, 11.2°±0.2°, 11.6°±0.2°, 11.8°±0.2°, 12.1°±0.2°, 13.1°±0.2°, 13.5°±0.2°, 15.1°±0.2°, 17.0°±0.2°, 18.1°±0.2°, 18.4°±0.2°, 18.9°±0.2°, 19.1°±0.2°, 19.9°±0.2°, 20.5°±0.2°, 20.9°±0.2°, 21.8°=0.2°, 22.6°±0.2°, 23.2°±0.2°, 23.9°±0.2°, 24.7°±0.2°, 25.1°±0.2°, 27.6°±0.2°, and 28.1°±0.2°;

the crystalline form H of Fingolimod embonate has an X-ray powder diffraction pattern comprising characteristic peaks at 2θ of 3.3°±0.2°, 5.0°±0.2°, 6.7±0.2°, 7.3°±0.2°, 10.1°±0.2°, 13.7°±0.2°, 17.2°±0.2°, 18.8°±0.2°, 20.3°±0.2°, 20.6°±0.2°, 21.8°±0.2°, 22.2°±0.2°, 23.7°±0.2°, and 27.7°±0.2°;

the crystalline form K of Fingolimod embonate has an X-ray powder diffraction pattern comprising characteristic peaks at 2θ of 3.4°±0.2°, 6.7°±0.2°, 7.3±0.2°, 10.2°±0.2°, 10.5°±0.2°, 13.1°±0.2°, 13.8°±0.2°, 16.3°±0.2°, 17.0°±0.2°, 17.4°±0.2°, 17.9°±0.2°, 18.2°±0.2°, 18.9°±0.2°, and 20.4°±0.2°;

the crystalline form 1 of Fingolimod 1-hydroxy-2-naphthoate has an X-ray powder diffraction pattern comprising characteristic peaks at 2θ of 3.2°±0.2°, 9.6°±0.2°, 12.9°±0.2°, 16.1°±0.2°, 19.4°±0.2°, 25.9°±0.2°, 29.3°±0.2°, and 36.0°±0.2°.

6. The crystalline form of the salt of Fingolimod according to claim 1, wherein:

the crystalline form B of Fingolimod embonate has an X-ray powder diffraction pattern substantially shown in FIG. 1;

the crystalline form A of Fingolimod embonate has an X-ray powder diffraction pattern substantially shown in FIG. 4;

the crystalline form I of Fingolimod embonate has an X-ray powder diffraction pattern substantially shown in FIG. 8;

the crystalline form J of Fingolimod embonate has an X-ray powder diffraction pattern substantially shown in FIG. 9;

the crystalline form C of Fingolimod embonate has an X-ray powder diffraction pattern substantially shown in FIG. 10;

the crystalline form D of Fingolimod embonate has an X-ray powder diffraction pattern substantially shown in FIG. 11;

the crystalline form E of Fingolimod embonate has an X-ray powder diffraction pattern substantially shown in FIG. 12;

the crystalline form F of Fingolimod embonate has an X-ray powder diffraction pattern substantially shown in FIG. 13;

the crystalline form G of Fingolimod embonate has an X-ray powder diffraction pattern substantially shown in FIG. 14;

the crystalline form H of Fingolimod embonate has an X-ray powder diffraction pattern substantially shown in FIG. 15;

the crystalline form K of Fingolimod embonate has an X-ray powder diffraction pattern substantially shown in FIG. 16; and the crystalline form 1 of Fingolimod 1-hydroxy-2-naphthoate has an X-ray powder diffraction pattern substantially shown in FIG. 17.

7. The pharmaceutical composition according to claim 2, wherein the pharmaceutical composition comprises:

(a) the therapeutically and/or prophylactically effective amount of the crystalline form of the salt of Fingolimod;

(b) polyethylene glycol 4000;

(c) poloxamer;

(d) disodium hydrogen phosphate;

(e) sodium dihydrogen phosphate; and (f) water for injection.

8. The pharmaceutical composition according to claim 7, wherein the pharmaceutical composition further comprises sodium hydroxide or hydrochloric acid.

9. A crystalline form of a salt of Fingolimod of formula I:

I

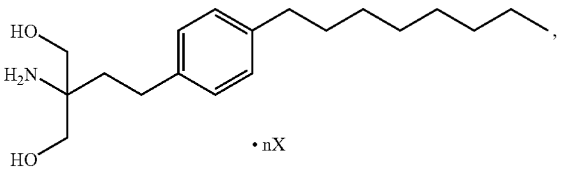

wherein X is embonic acid or 1-hydroxy-2-naphthoic; and the crystalline form is a crystalline form 1 of Fingolimod 1-hydroxy-2-naphthoate, which is an anhydrate, has an X-ray powder diffraction pattern comprising characteristic peaks at 2θ of 3.2°±0.2°, 9.6°±0.2°, 12.9°±0.2°, 16.1°±0.2°, 19.4°±10.2°, and 25.9°±0.2°, and a molar ratio of Fingolimod to 1-hydroxy-2-naphthoic acid of 1:1.

10. The crystalline form of the salt of Fingolimod according to claim 9, wherein the X-ray powder diffraction pattern comprises characteristic peaks at 2θ of 3.2°±0.2°, 9.6°±0.2°, 12.9°±0.2°, 16.1°±0.2°, 19.4°±0.2°, 25.9°±0.2°, 29.3°±0.2°, and 36.0°±0.2°.

11. A pharmaceutical composition, comprising a therapeutically and/or prophylactically effective amount of the crystalline form of the salt of Fingolimod according to claim 9 and a pharmaceutically acceptable auxiliary material.

12. A pharmaceutical composition comprising:

(a) the crystalline form 1 of Fingolimod 1-hydroxy-2-naphthoate according to claim 9;

(b) polyethylene glycol 4000;

(c) poloxamer;

(d) disodium hydrogen phosphate;

(e) sodium dihydrogen phosphate; and (f) water for injection.

* * * * *